United States Patent

Slusarek et al.

[11] Patent Number: 6,153,369
[45] Date of Patent: *Nov. 28, 2000

[54] PHOTOGRAPHIC ELEMENT CONTAINING PYRAZOLONE PUG RELEASING COUPLER AND IMAGING PROCESS EMPLOYING SAME

[75] Inventors: Wojciech K. Slusarek; Jerrold N. Poslusny, both of Rochester; Xiqiang K. Yang, Webster, all of N.Y.

[73] Assignee: Eastman Kodak Company, Rochester, N.Y.

[*] Notice: This patent is subject to a terminal disclaimer.

[21] Appl. No.: 09/224,232

[22] Filed: Dec. 30, 1998

[51] Int. Cl.$^7$ .............................. G03C 1/08; G03C 7/26; G03C 7/32
[52] U.S. Cl. .................... 430/555; 430/544; 430/955; 430/956; 430/957; 430/958; 430/959; 430/960
[58] Field of Search .................................. 430/543, 555, 430/955, 956, 957, 958, 959, 960, 544

[56] References Cited

U.S. PATENT DOCUMENTS

| | | | |
|---|---|---|---|
| 3,419,391 | 12/1968 | Young | 430/543 |
| 4,686,175 | 8/1987 | Ogawa et al. | 430/555 |
| 4,985,336 | 1/1991 | Ichijima et al. | 430/555 |
| 5,576,167 | 11/1996 | Poslusny et al. | 430/555 |
| 5,670,306 | 9/1997 | Poslusny et al. | 430/555 |

*Primary Examiner*—Geraldine Letscher
*Attorney, Agent, or Firm*—Arthur E. Kluegel

[57] ABSTRACT

Disclosed is a photographic element comprising a light-sensitive silver halide emulsion layer having associated therewith a pyrazol-5-one coupler bearing a 4-aryloxy coupling-off group containing a group capable of releasing a photographically useful group (PUG) wherein:

(1) the pyrazol-5-one ring contains a 1-aryl substituent which in turn contains, in a position ortho to the bond linking it to the pyrazolone ring, a secondary carbon-amido group or a secondary sulfonamido group;

(2) the pyrazol-5-one ring contains either (a) a 3-aryl substituent which in turn contains substituents for which the sum of the Hammett's σ constant values is −0.3 or higher or (b) a 3-alkyl substituent; and (3) the 4-aryloxy coupling-off group:
  (a) contains ring substituents selected so that the sum of the Hammett's σ constant values for all substituents on the phenoxy ring is at least 0.4 but does not contain a nitro substituent in the ortho position, and:
  (b) contains in at least one position ortho or para to the oxygen atom bonding the aryloxy group to the pyrazolone ring a substituent comprising a tetrahedral carbon atom bonded to a PUG or to another timing group which timing group is in turn bonded to a PUG directly or through a further timing group; and provided that substituents may join to form one or more additional rings.

18 Claims, No Drawings

PHOTOGRAPHIC ELEMENT CONTAINING PYRAZOLONE PUG RELEASING COUPLER AND IMAGING PROCESS EMPLOYING SAME

FIELD OF THE INVENTION

This invention relates to a photographic element having a light-sensitive silver halide emulsion layer having associated therewith a stable 1-aryl-3-aryl-4-aryloxypyrazol-5-one or a 1-aryl-3-alkyl-4-aryloxypyrazol-5-one based magenta coupler which is capable of releasing a certain timing group which is capable of releasing either a photographically useful group or a further timing group which in turn is capable of releasing a photographically useful group.

BACKGROUND OF THE INVENTION

In a silver halide photographic element, a color image is formed when the material is exposed to light and then developed using a primary amine color developer. The development results in imagewise reduction of silver halide and the corresponding production of oxidized developer. The oxidized developer then reacts in an imagewise fashion with one or more incorporated dye-forming couplers to form a dye image. At the same time, it is common that at least one of the couplers present in the photographic element be capable of releasing a group capable of affecting the photographic properties of the resulting image. In such cases, a portion of the coupler referred to as the "coupling-off group" is released during the coupling process and this in turn affects the resulting image in a predetermined manner.

Magenta dye-forming couplers are employed in subtractive color forming processes. One of the principal coupler types useful for this purpose are those based on a pyrazolone ring. Pyrazolone-based couplers having a coupling-off group linked to the pyrazolone ring by oxygen have long been considered as potentially attractive two equivalent magenta couplers. An oxygen-linked coupling-off group could impart increased activity to the pyrazolone coupler; however the general instability of these couplers toward ambient oxygen makes them difficult to synthesize and impractical for use in a film environment since they decompose during keeping therby reducing the density of the dye formed upon exposure and processing. In particular, pyrazolone couplers having an anilino or acylamino substituent at the 3-position have exhibited unacceptable stability when an aryloxy is employed as a coupling-off group. As a result, pyrazolone couplers have employed either so-called "four equivalent" couplers containing hydrogen at the coupling-off position or have employed so-called "two-equivalent" couplers containing a coupling-off group having a sulfur or nitrogen atom linked to the pyrazolone ring. Such couplers have been employed as image couplers where the primary purpose is to form image dye or as image modifying couplers whose primary purpose is to modify the ultimate image to enhance sharpness, granularity, etc.

U.S. Pat. No. 3,419,391 discloses certain types of pyrazolone-based compounds as two-equivalent couplers having high dye-forming reactivity and reduced tendency to form color fog. This is not related to keeping requirements. According to the patent, the pyrazolone ring is not limited to the presence of any particular substituents at the 3-position or elsewhere. Specifically identified substituents at the 3-position include anilino, acylamino, alkyl, amino, alkoxy, amido, carbamoyl, ureido, thio, guanidino, etc. The couplers of the patent may contain an aryl group at the 1-position and, among other things, an alkyl or carboxy ester group at the 3-position. The aryloxy couplers of the patent are said not to produce color fog (printout) and to provide improved reactivity. Thus, they are said to provide low printout or yellowing in Dmin areas when they are exposed to light or high temperatures, respectively, subsequent to development. No mention is made of the poor keeping of pyrazolone couplers having aryloxy coupling-off groups although their instability is well known in the art.

U.S. Pat. No. 4,985,336 discloses a photographic element containing in a green sensitive layer a precursor compound capable of releasing a compound upon reacting with an oxidation product of a developing agent and said released compound is capable of releasing a development inhibitor upon further reacting with another molecule of oxidized developing agent. Several compounds exemplified have a phenoxy coupling-off group with a para nitro and a release group in the ortho position but the presence of a methyl group in the 3-position of the pyrazolone ring does not provide the requisite keeping.

U.S. Pat. No. 5,670,306 discloses a class of pyrazolone-containing compounds as two-equivalent couplers having adequate dye-forming reactivity and good keeping. These compounds, featuring a mono-, di-, or tri-substituted carbon atom at the 3-position of the pyrazolone ring were difficult to prepare, requiring multi-step syntheses.

U.S. Pat. No. 4,686,175 discloses a coupler D-29 which incorporates a 1-aryl-3-aryl-4-aryloxypyrazolone DIR coupler. The inhibitor release mechanism is an intramolecular displacement group the synthesis of which employs phosgene and would be difficult to synthesize. Further, the example contains only a para substituent on the 1-aryl ring.

It would be useful to provide a photographic element that is stable during synthesis, film manufacture, and during film keeping, that would provide for the effective release of a photographically useful group, and which would be straightforward to prepare. It would be desirable to have a compound possessing all of the above attributes that would, in addition, be crystalline and therefore more easily manufacturable. This compound would advantageously display an improved keeping stability.

SUMMARY OF THE INVENTION

The invention provides a photographic element comprising a light-sensitive silver halide emulsion layer having associated therewith a pyrazol-5-one coupler bearing a 4-aryloxy coupling-off group containing a group capable of releasing a photographically useful group (PUG) wherein:

(1) the pyrazol-5-one ring contains a 1-aryl substituent which in turn contains, in a position ortho to the bond linking it to the pyrazolone ring, a secondary carbonamido group or a secondary sulfonamido group;

(2) the pyrazol-5-one ring contains either (a) a 3-aryl substituent which in turn contains substituents for which the sum of the Hammett's σ constant values is –0.3 or higher or (b) a 3-alkyl substituent; and (3) the 4-aryloxy coupling-off group:
  (a) contains ring substituents selected so that the sum of the Hammett's σ constant values for all substituents on the phenoxy ring is at least 0.4 but does not contain a nitro substituent in the ortho position, and:
  (b) contains in at least one position ortho or para to the oxygen atom bonding the aryloxy group to the pyrazolone ring a substituent comprising a tetrahedral carbon atom bonded to a PUG or to another timing group which timing group is in turn bonded to a PUG directly or through a further timing group; and provided that substituents may join to form one or more additional rings.

The element of the invention may be represented by the following formula:

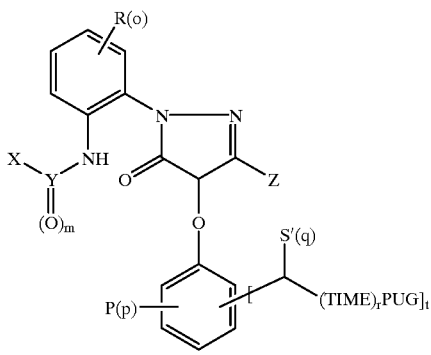

wherein:

X represents an aryl, alkyl, alkylamino or arylamino group;

Y can be carbon or sulfur; m is 1 when Y is carbon and 2 when Y is sulfur;

R represents a halogen or an alkyl group; and o is 0 to 4; provided that two or more R substituents may join to form one or more additional rings;

Z is either (a) an aryl group represented as $Ar^3Q(n)$ wherein Q represents n independently selected substituents bonded to the $Ar^3$ ring, provided that the sum of the Hammett's σ constant values for all Q substituents is −0.3 or higher and n is 0 to 5 and provided further that two or more Q substituents may join to form one or more additional rings or (b) an alkyl group;

P represents p independently selected substituents bonded to the aryloxy ring, provided that the sum of the Hammett's σ constant values for all P substituents is at least 0.4, and provided further that P may not be a nitro group ortho to the oxygen atom linking the aryloxy group to the 4 position of the pyrazolone ring and p is 1 to 4, provided that two or more P substituents may join to form one or more additional rings;

each PUG containing substituent is located in a position ortho or para to the oxygen atom bonding the aryloxy group to the pyrazolone ring and t is 1 or 2;

each TIME group is independently a timing group; each r is independently 0 or 1; and each PUG is independently a photographically useful group;

S' represents q independently selected alkyl or aryl groups and q is 0 to 2, provided that two S' groups or an S' and a P group may join to form a ring; and provided further that X and an R group may join to form an additional ring.

The invention also provides a process for forming an image in an element of the invention.

Photographic elements incorporating the coupler of the invention form a magenta dye upon coupling and effect the timed release of a photographically useful group while providing improved stability during synthesis, film manufacture and keeping.

DETAILED DESCRIPTION OF THE INVENTION

The aryl group identified at the 1-position, the alkyl or aryl groups identified at the 3-position, and the aryloxy group identified at the 4-position of the pyrazolone ring are independently selected.

In the case where phenyl is selected as an aryl group in the 3-position, it is believed, based on the results of testing, that the proper selection of substituents for this 3-phenyl group can be accomplished by calculating the sum of the Hammett's σ constant values for all of the 3-phenyl ring substituents such that the sum of the σ constant values for all ring substituents ($\sigma_p$ for an ortho or para position or $\sigma_m$ for a meta position depending on the location of each said ring substituent group relative to the carbon atom linking the phenyl ring to the pyrazolone ring) is −0.3 or higher. See "Survey of Hammett Substituent Constants and Resonance Field Parameters", C. Hansch, A. Leo, and R. Taft, Chem. Rev., 91, 165–195, (1991), for a definition of the terms and for a table of constant values for various substituents.

In the case where phenoxy is selected as an aryloxy group in the 4-position, it is believed, based on the results of testing, that the proper selection of substituents for this 4-phenoxy group can be accomplished by calculating the sum of the Hammett's σ constant values for all of the phenoxy ring substituents. Because the 4-phenoxy ring is an electron rich group, at least one substituent is needed independently selected from the groups usable as substituents described herein provided that there are among the ring substituent groups sufficient electron withdrawing capacity such that the sum of the Hammett's constant values (Σσ) for all ring substituents ($\sigma_p$ for an ortho or para position or $\sigma_m$ for a meta position depending on the location of each said ring substituent group relative to the oxygen atom linking the phenyl ring to the pyrazolone ring) is at least 0.40. See "Survey of Hammett Substituent Constants and Resonance Field Parameters", cited above, for a definition of the terms and for a table of constant values for various substituents.

In the more general case where additional benzene ring(s) are fused to the 3-phenyl group, an adjustment factor may be required in determining the Σσ in accordance with the number of additional rings. Such adjustment values are given for example in Table 7.1 of D .D. Penin, B. Dempsey and E. P. Serjeant "$pK_a$ Prediction for Organic Acids and Bases", Chapman and Hall, London and New York, (1981) p 67. Thus, in the case where there is no substituent on the 3-phenyl ring, the fused carboaromatic system itself must provide a σ adjustment factor so that the total for the ring is −0.30 or higher. Otherwise, an electron withdrawing substituent is necessary.

In the more general case where additional benzene ring(s) are fused to the 4-phenoxy group, an adjustment factor may be required in determining the Σσ in accordance with the number of additional rings. Such adjustment values are given for example in Table 7.1 of the "$pK_a$ Prediction for Organic Acids and Bases" as cited above. Thus, in the case where there is no substituent on the 4-phenoxy ring other than that containing the photographically useful group (PUG), the fused carboaromatic system itself must provide a C adjustment factor so that the total for the ring exceeds the required 0.4. Otherwise, an electron withdrawing substituent is necessary. Since positive σ values represent electron withdrawing character and since the value for hydrogen is 0, it follows that a sum of 0.4 can only be achieved by the presence of at least one electron withdrawing group.

Examples of electron withdrawing substituents, useful in attenuating the electron density of 3-arylyl and 4-aryloxy rings include halogen, —$NO_2$, —CN, —NR'$SO_2$R", —NR'C(O)R", —C(O)N(R)R", —C(O)OR', —OC(O)R', —C(O)R', —OSO₂R', —SO₂R', —SO₂N(R')R", —SO₂OR' and halogenated alkyl such as —CF₃ wherein each R' and R" is independently hydrogen or a substituent group. Examples of suitable specific substituents include the following: sulfamoyl, such as N-methylsulfamoyl, N-hexadecylsulfamoyl, N,N-dimethylsulfamoyl; N-[3-(dodecyloxy)propyl]sulfamoyl, N-[4-(2,4-di-t-pentylphenoxy)butyl]-sulfamoyl, N-methyl-N-tetradecylsulfamoyl, and N-dodecylsulfamoyl; sulfamido, such as hexadecylsulfamido and N-octadecylmethylsulfamido; carbamoyl, such as N-methylcarbamoyl, N-octadecylcarbamoyl, N-[4-(2,4-di-t-pentylphenoxy)butyl]carbamoyl, N-methyl-N-tetradecylcarbamoyl, and N,N-dioctylcarbamoyl; diacylamino, such as N-succinimido, N-phthalimido, 2,5-dioxo-1-oxazolidinyl, 3-dodecyl-2,5-dioxo-1-imidazolyl, and N-acetyl-N-dodecylamino; aryloxycarbonyl, such as phenoxycarbonyl and p-dodecyloxyphenoxy carbonyl; alkoxycarbonyl, such as alkoxycarbonyl containing 2 to 30 carbon atoms, for example methoxycarbonyl, tetradecyloxycarbonyl, ethoxycarbonyl, phenoxycarbonyl, benzyloxycarbonyl, and dodecyloxycarbonyl; alkoxysulfonyl, such as alkoxysulfonyl containing 1 to 30 carbon atoms, for example methoxysulfonyl, octyloxysulfonyl, tetradecyloxysulfonyl, and 2-ethylhexyloxysulfonyl; aryloxysulfonyl, such as phenoxysulfonyl, 2,4-di-t-pentylphenoxysulfonyl; alkanesulfonyl, such as alkanesulfonyl containing 1 to 30 carbon atoms, for example methanesulfonyl, octanesulfonyl, 2-ethylhexanesulfonyl, and hexadecanesulfonyl; arenesulfonyl, such as benzenesulfonyl, 4-nonylbenzenesulfonyl, and p-toluenesulfonyl. Sulfinyl and sulfoxyl compounds corresponding to the foregoing sulfonyl compounds are also suitable.

It is essential that the 4-aryloxy group not include a nitro group ortho to the oxygen atom linking the aryl ring to the pyrazolone ring. The exclusion of ortho nitro is necessitated by its very strong destabilizing effect on the corresponding pyrazolone couplers which leads to their very rapid decomposition. Such combination provides an unstable coupler which fails to perform the desired PUG release during processing or releases the PUG during storage to cause nonimagewise results.

The use of a 3-aryl group generally presents a problem in the case of couplers for which the primary purpose is to form an image because of hue considerations. The couplers of the present invention have for their primary purpose the release of a photographically useful group (PUG). These couplers are typically employed in far lower coating laydowns than is the case with imaging couplers. While it is desirable to employ a coupler which forms dye of satisfactory hue, it is more important to obtain the maximum amount of dye formation without sacrificing keeping ability and PUG releasing capability of these types of couplers. The precise hue is less significant since the portion of the image contributed by the PUG releasing coupler is relatively insignificant. In other words, the color related features are not as important for a PUG releasing coupler as they are for an imaging coupler.

The 4-phenoxy group of the invention functions as a timing group and suitably has the following formula:

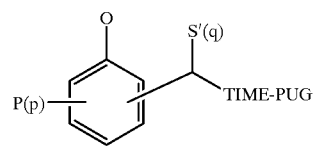

wherein PUG is a photographically useful group such as an inhibitor, P is an electron withdrawing group such as nitro, cyano, alkylsulfonyl; sulfamoyl (—SO₂N(R')R"); and sulfonamido (—NR'SO₂R") groups wherein each R' and R" is independently hydrogen or a substituent; S' is an alkyl or aryl group; and TIME is a timing group; q is 0 or 1, and p is 1 to 2. The oxygen atom is bonded to the 4-position of the 1-phenyl-3-arylpyrazol-5-one coupler.

Two of the 3-phenyl ring substituents Q or 4-phenoxy ring substituents P may be joined by an alkylene bridge —[C(R$_x$)₂]$_n$— to form an additional ring; each R, is independently hydrogen, alkyl or aryl and n is 0 to 3. A ring can also form in the same manner by combining a P substituent and an S' substituent of the 4-phenoxy group. It is required that when two substituents are joined by a link (n is 0) then one of them ought to be an alkyl group. In all three instances (P—P, Q—Q, and P—S'), the required values of σ can be determined by breaking the alkylene bridge and treating the resulting fragments as two separate substituents. The separate values of σ for both fragments are then added for use in computing σ. When two substituents are linked (n is 0) or when an alkylene group (n is 1) bridges two substituents, it may be necessary, for the sake of computing, to add an alkyl group to the link or bridge, so that both fragments, resulting from the rupture of the ring, will be capped by the same alkyl group.

Examples of suitable 4-aryloxy timing groups suitable for releasing PUGs of various types in accordance with the invention are as shown below. In all examples symbol (+) denotes the bond to the 4 position of the pyrazolone ring whereas symbol (++) denotes the bond to PUG:

T-1

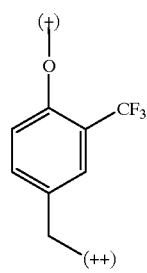

T-2

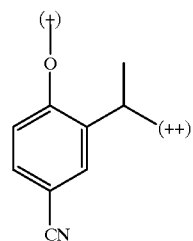

-continued
T-3
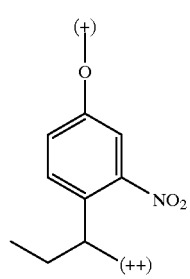
T-4
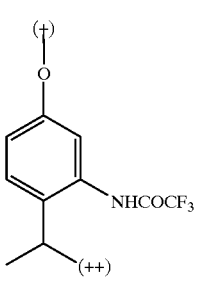
T-5
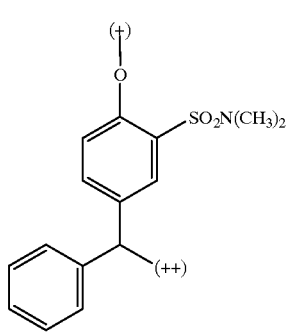
T-6
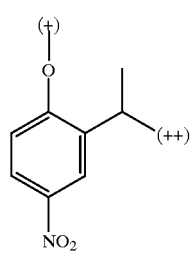
T-7
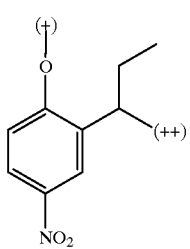
-continued
T-8
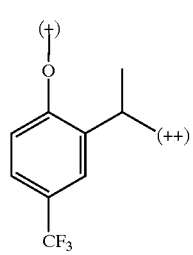
T-9
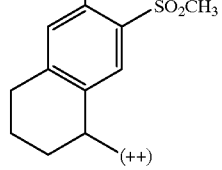
T-10
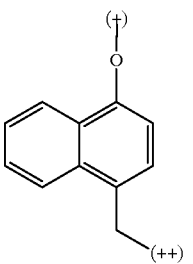
T-11
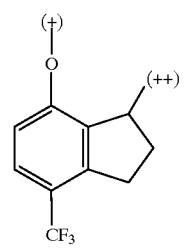
T-12
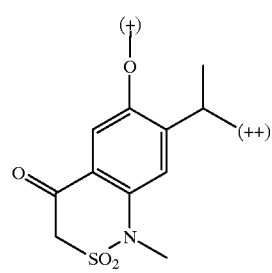
T-13

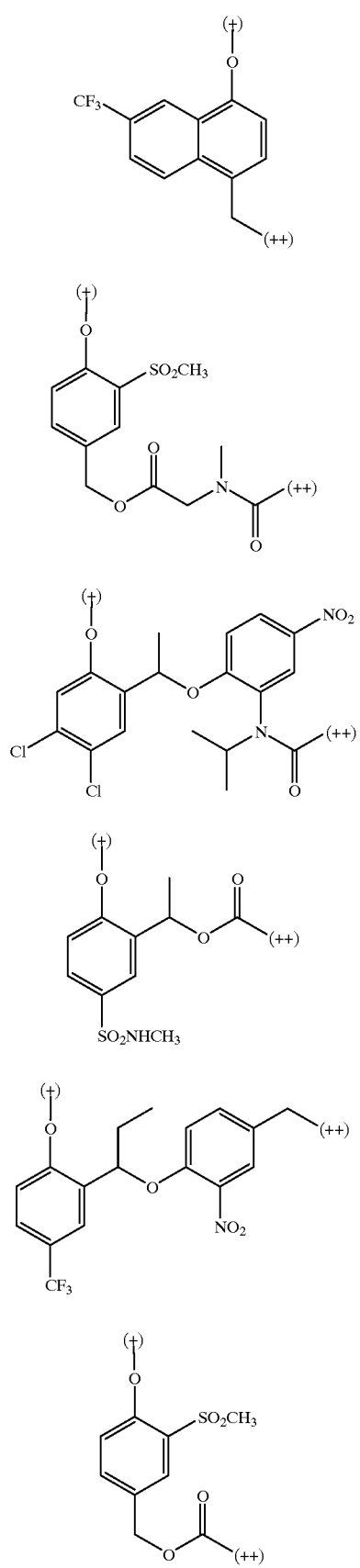

-continued

T-26

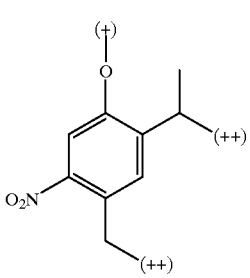

PUG can be any photographically useful group known in the art. For example, PUG can be a dye or dye precursor, such as a sensitizing dye, filter dye, image dye, leuco dye, blocked dye, shifted dye, or ultraviolet light absorber. Alternatively PUG can be a photographic reagent, which upon release can further react with components in the element. Such reagents include development accelerators or inhibitors, bleach accelerators or inhibitors, couplers (e.g. competing couplers, color-forming couplers, or DIR couplers), developing agents (e.g. competing developing agents or auxiliary developing agents), silver complexing agents, fixing agents, toners, hardeners, tanning agents, fogging agents, antifoggants, antistain agents, stabilizers, nucleophiles and dinucleophiles, and chemical or spectral sensitizers and desensitizers.

Examples of typical inhibitor moieties are: oxazoles, thiazoles, diazoles, triazoles, oxadiazoles, thiadiazoles, oxathiazoles, thiatriazoles, benzotriazoles, tetrazoles, benzimidazoles, indazoles, isoindazoles, mercaptotetrazoles, selenotetrazoles, mercaptobenzothiazoles, selenobenzothiazoles, mercaptobenzoxazoles, selenobenzoxazoles, mercaptobenzimidazoles, selenobenzimidazoles, benzodiazoles, mercaptooxazoles, mercaptothiadiazoles, mercaptothi azoles, mercaptotriazoles, mercaptooxadiazoles, mercaptodiazoles, mercaptooxathiazoles, telleurotetrazoles or benzisodiazoles. In a preferred embodiment, the inhibitor moiety or group is selected from the following formulas:

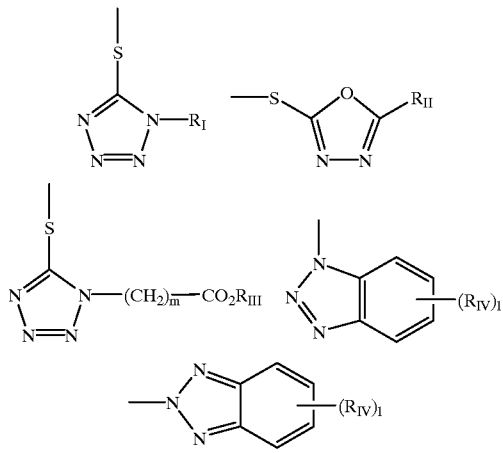

wherein $R_I$ is selected from the group consisting of straight and branched alkyls of from 1 to about 8 carbon atoms, benzyl, phenyl, and alkoxy groups and such groups containing none, one or more than one such substituent; $R_{II}$ is selected from $R_I$ and —$SR_I$; $R_{III}$ is a straight or branched alkyl group of from 1 to about 5 carbon atoms and m is from 1 to 3; and $R_{IV}$ is selected from the group consisting of hydrogen, halogens and alkoxy, phenyl and carbonamido groups, —$COOR_V$ and —$NHCOOR_V$ wherein $R_V$ is selected from substituted and unsubstituted alkyl and aryl groups, and I=1 to 4.

Examples of other PUGs are shown in the 1994 Research Disclosure cited hereinafter.

Coupler compounds in accordance with the invention are exemplified by the following examples with the corresponding values for the sum of the Hammett's (σ) constants being −0.30 for the 3-aryl ring and 0.4 for the 4-aryloxy ring:

D-1

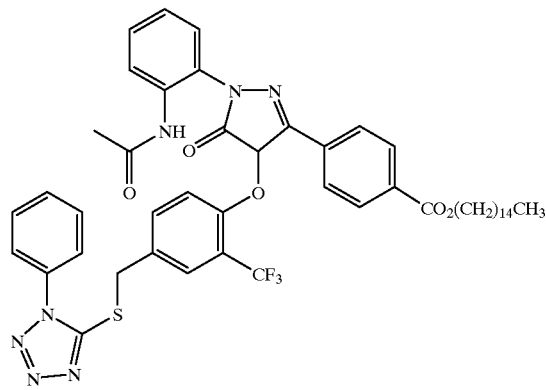

D-2

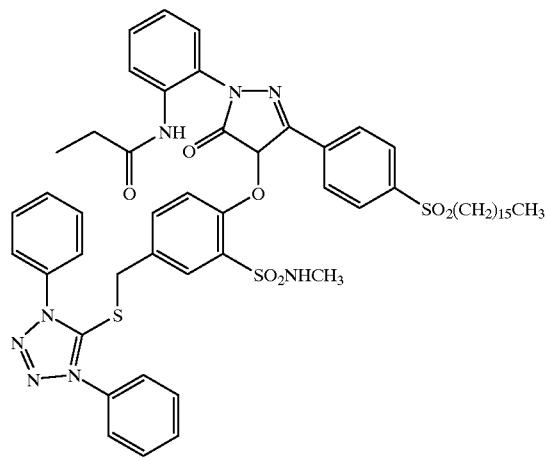

D-3

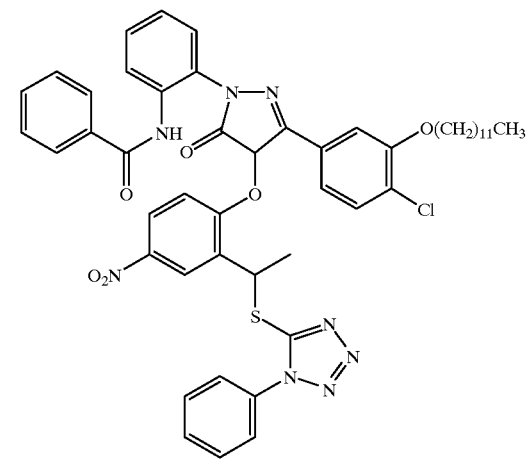

D-4
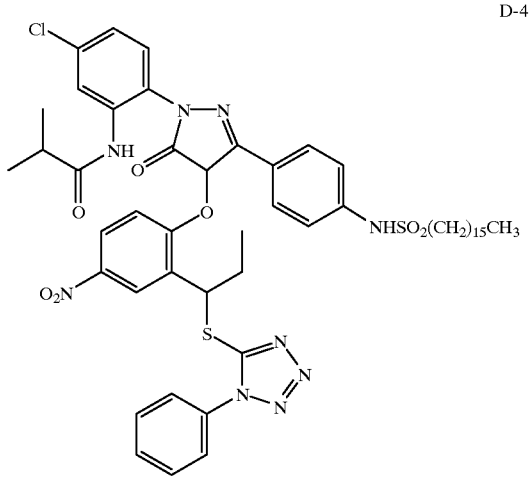
D-5
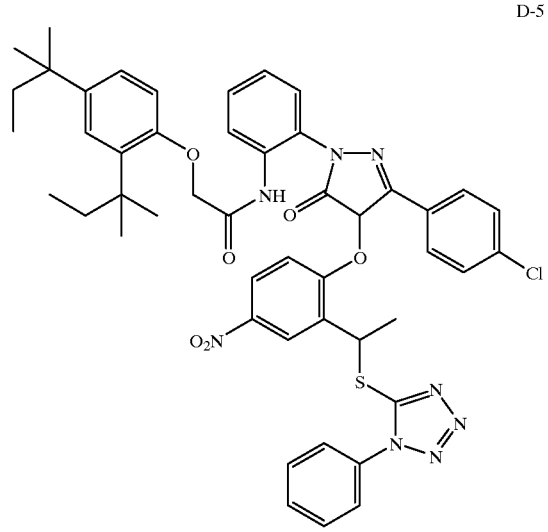
D-6
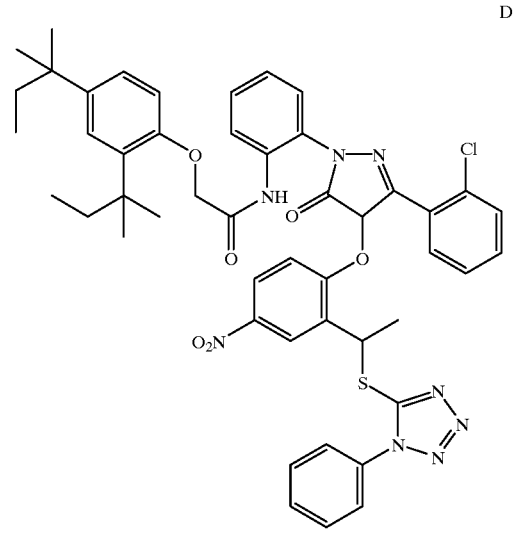
D-7
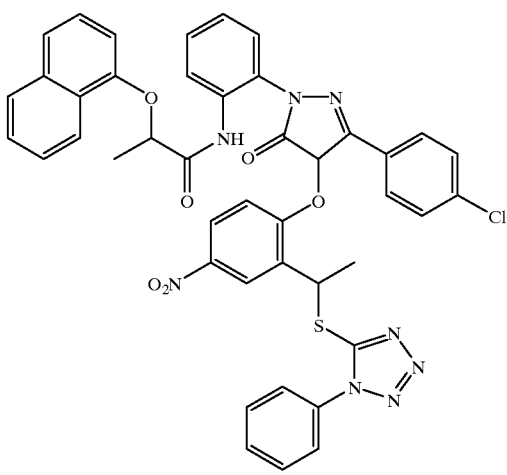
D-8
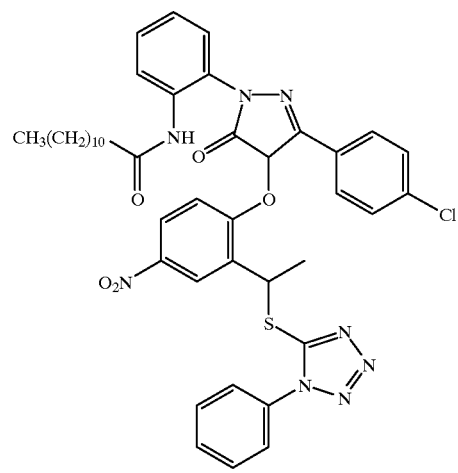
D-9
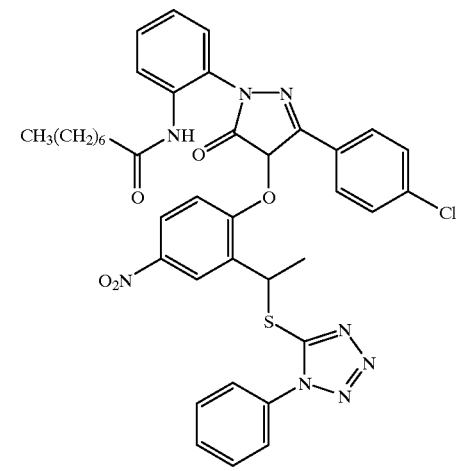

D-10
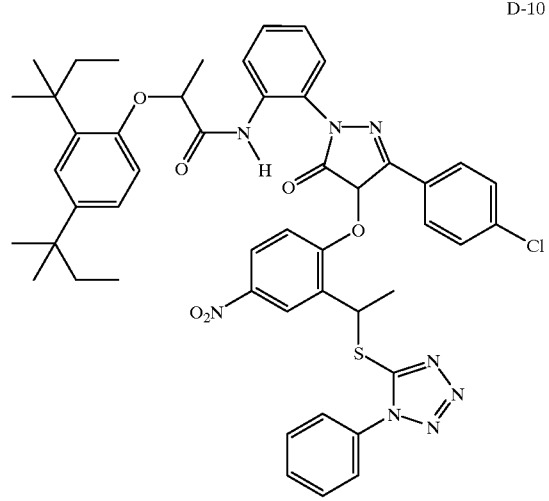
D-11
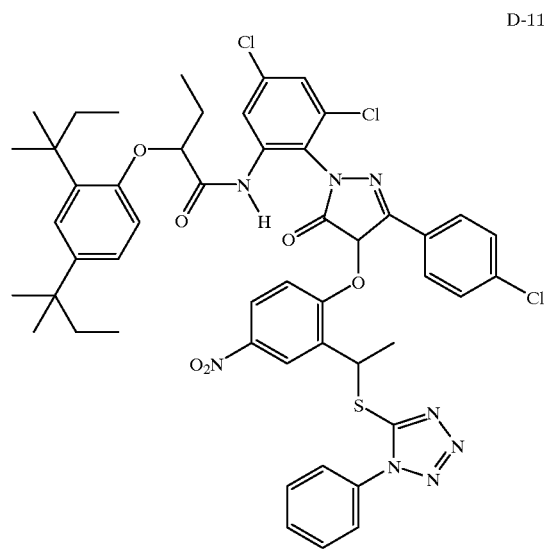
D-12
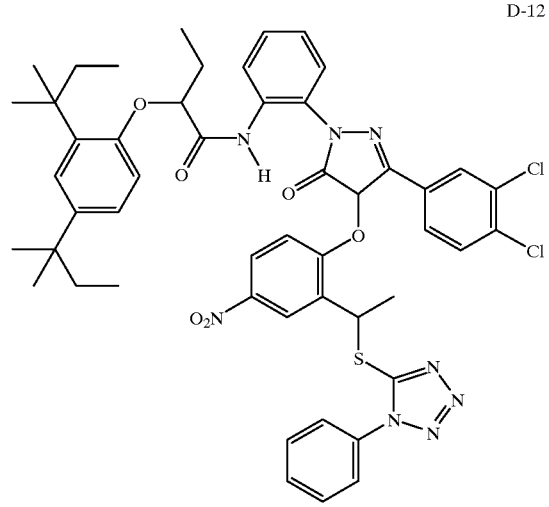
D-13
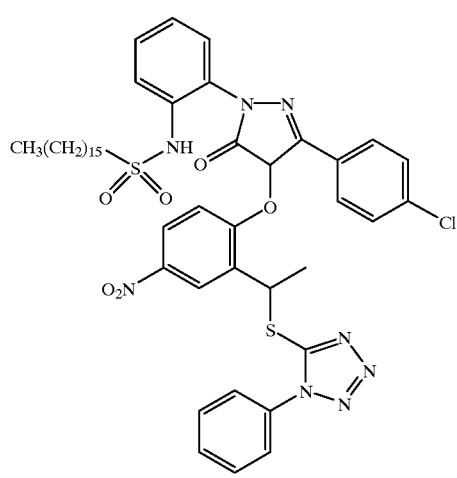
D-14
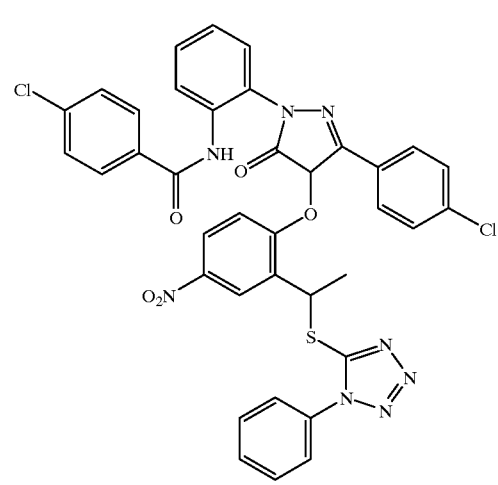
D-15
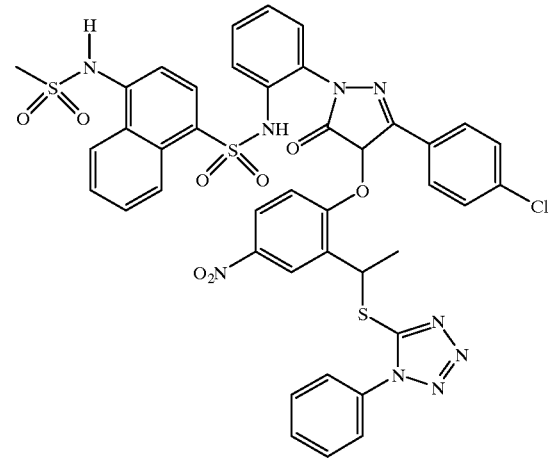

D-16
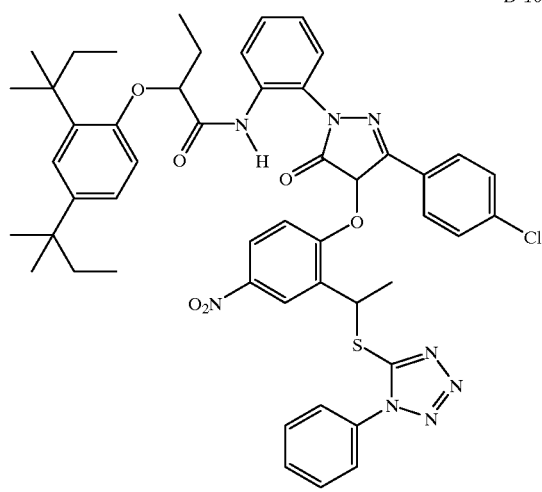
D-19
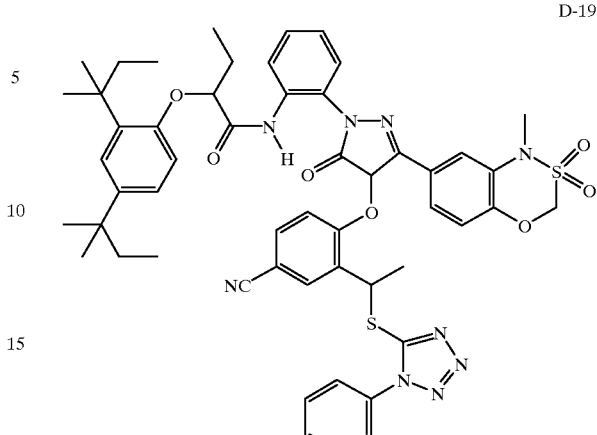
D-17
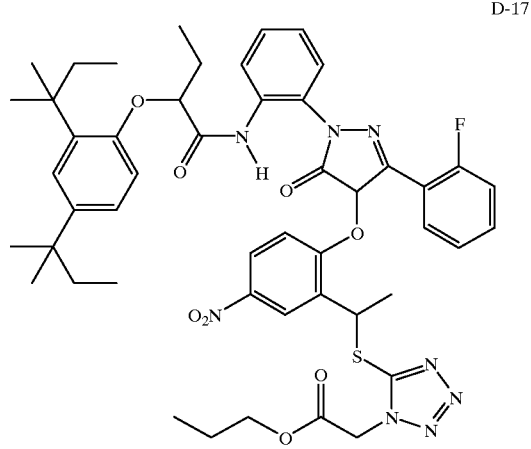
D-20
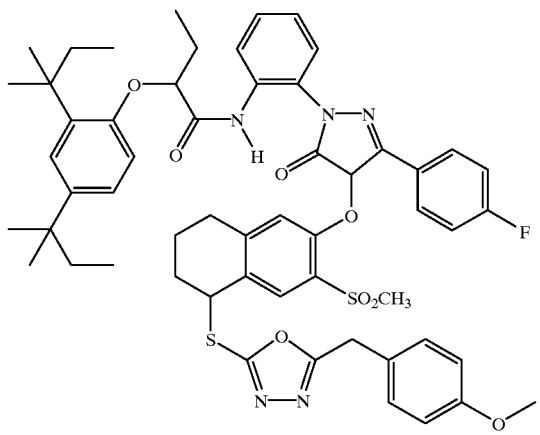
D-18
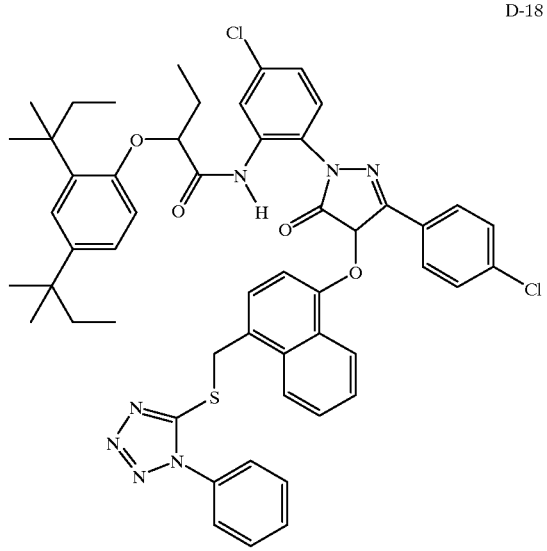
D-21
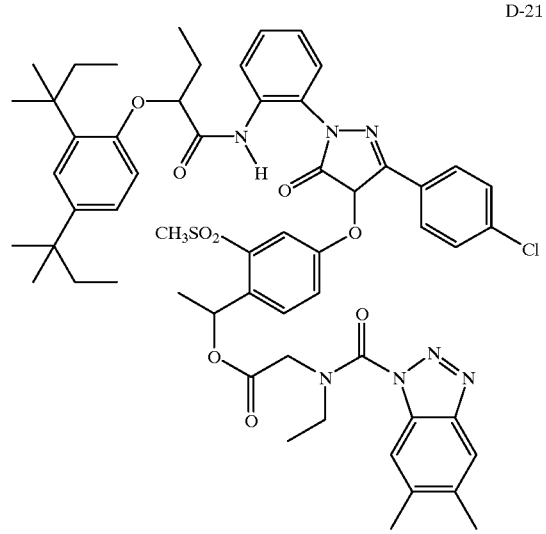

-continued
D-22
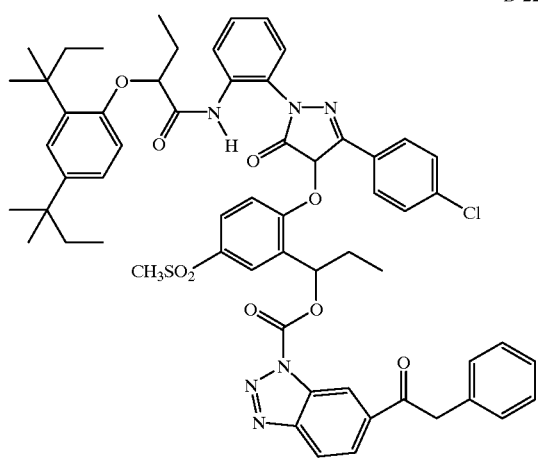
D-25
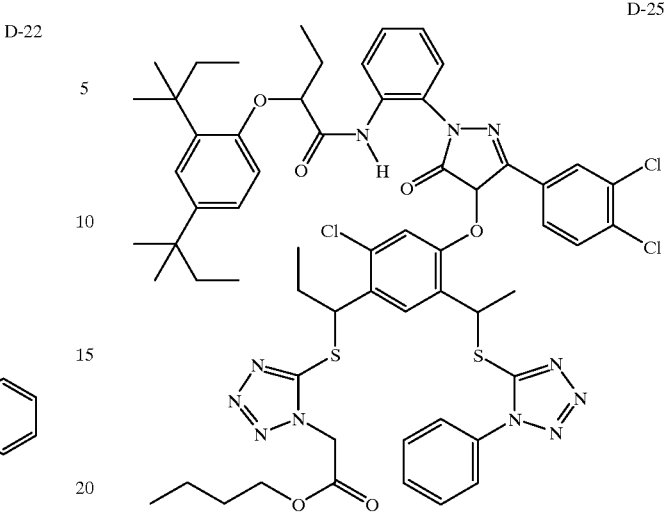
D-23
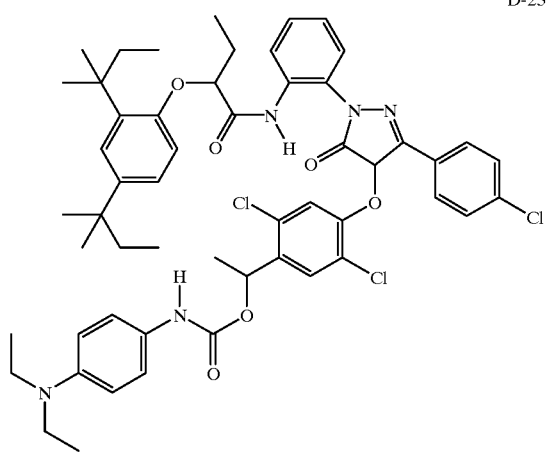
D-26
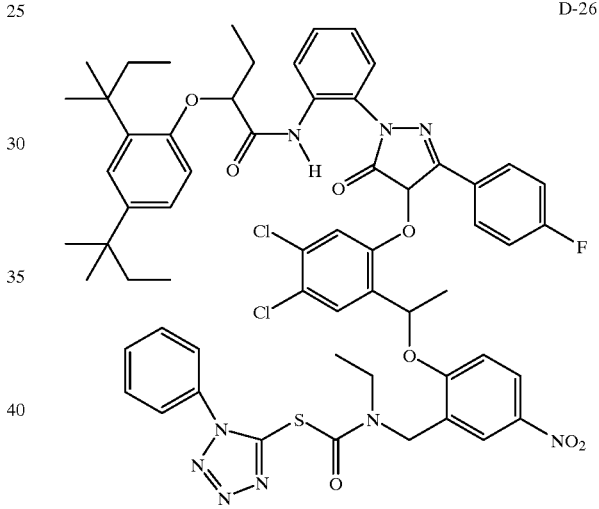
D-24
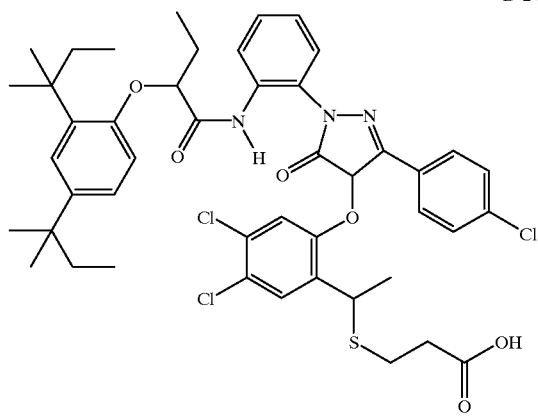
D-27
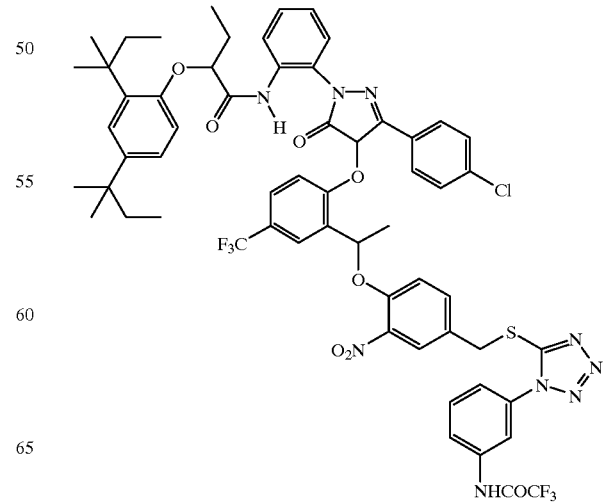

D-28
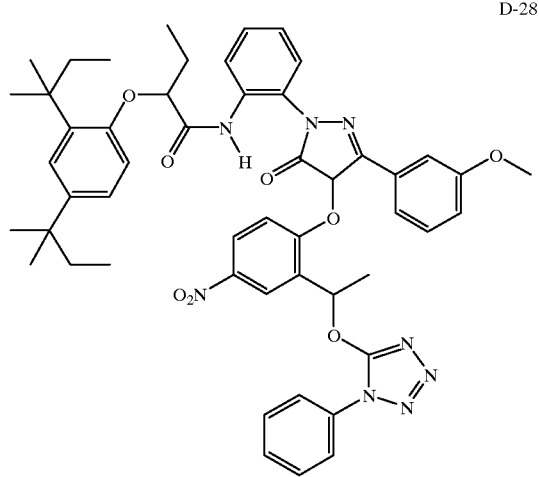
D-31
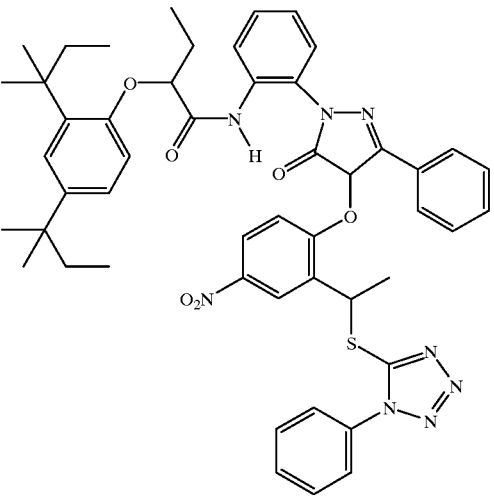
D-29
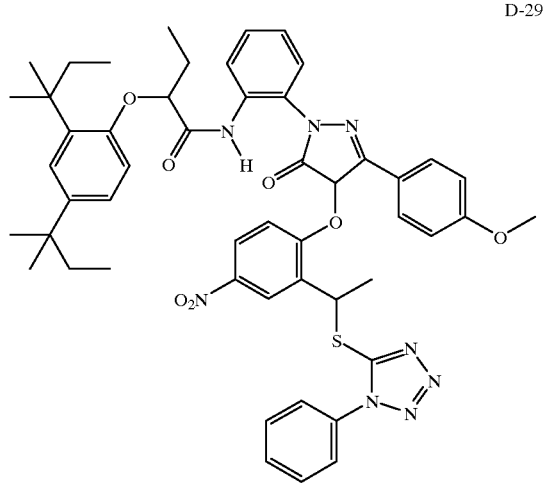
D-32
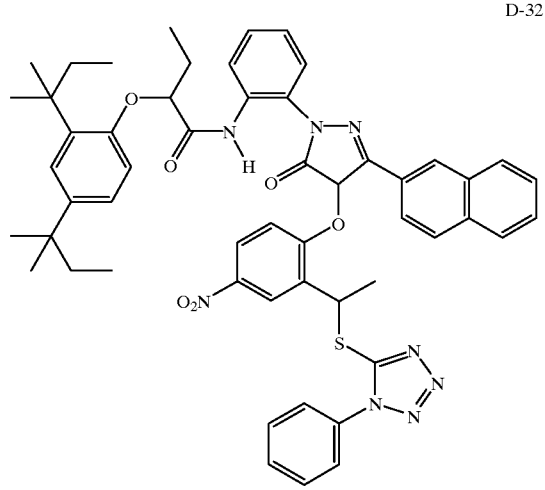
D-30
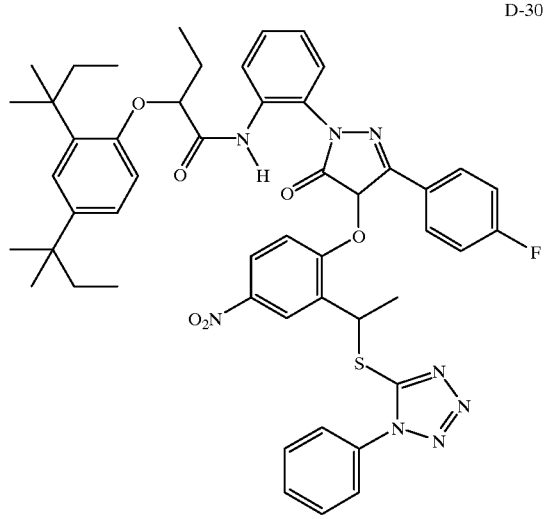
D-33
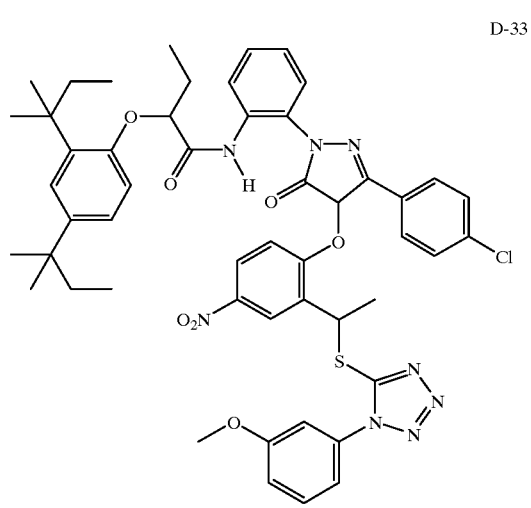

D-34
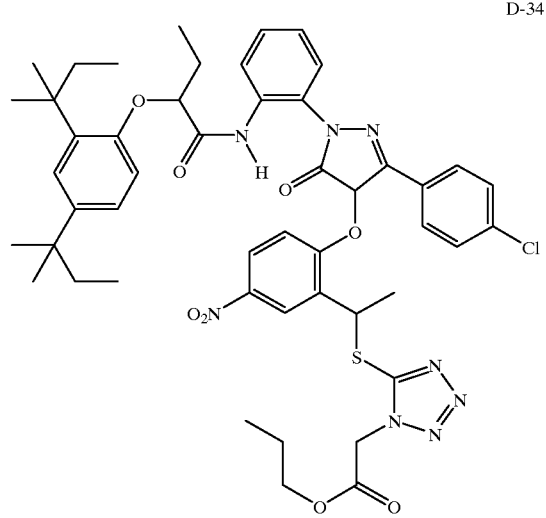
D-35
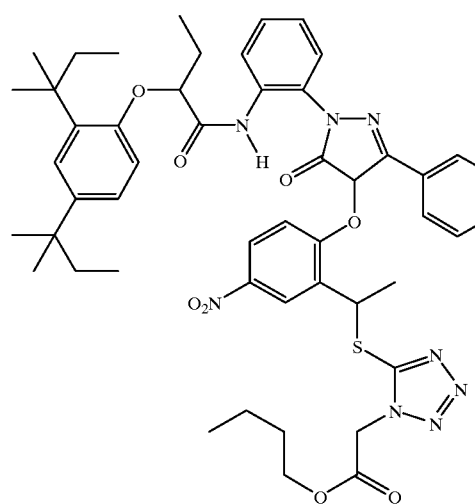
D-36
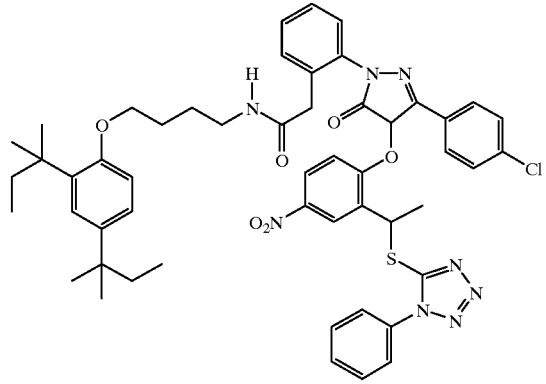
D-37
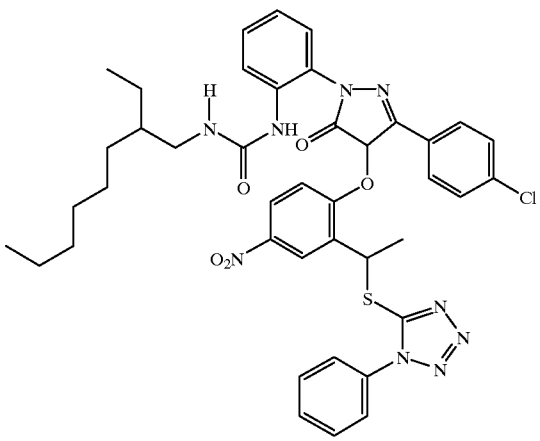
D-38
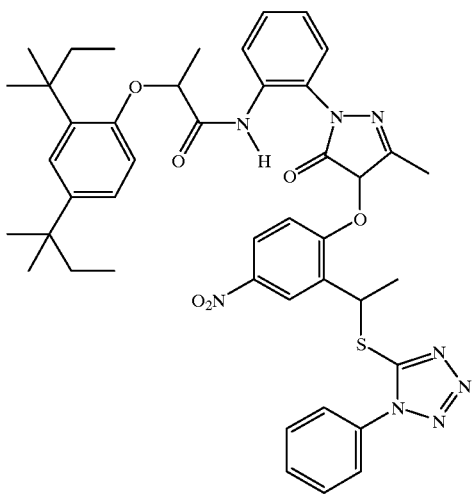
D-39
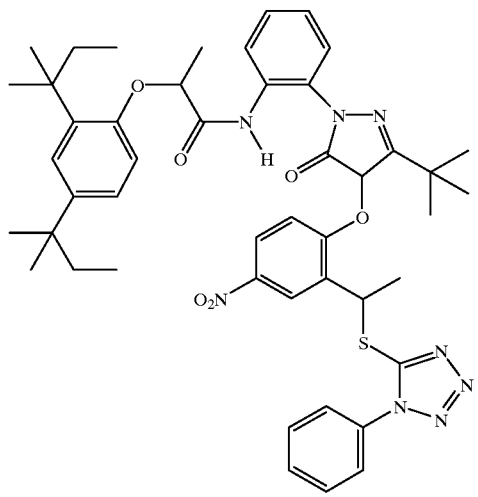

Unless otherwise specifically stated, use of the term "substituted" or "substituent" means any group or atom other than hydrogen. Additionally, when the term "group" is used, it means that when a substituent group contains a substitutable hydrogen, it is also intended to encompass not only the substituent's unsubstituted form, but also its form further substituted with any substituent group or groups as herein mentioned, so long as the substituent does not destroy properties necessary for photographic utility. Suitably, a substituent group may be halogen or may be bonded to the remainder of the molecule by an atom of carbon, silicon, oxygen, nitrogen, phosphorous, or sulfur. The substituent may be, for example, halogen, such as chlorine, bromine or fluorine; nitro; hydroxyl; cyano; carboxyl; or groups which may be further substituted, such as alkyl, including straight or branched chain or cyclic alkyl, such as methyl, trifluoromethyl, ethyl, t-butyl. 3-(2,4-di-t-pentylphenoxy) propyl, and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy)ethoxy, and 2-dodecyloxyethoxy; aryl such as phenyl, 4-t-butylphenyl, 2,4,6-trimethylphenyl, naphthyl; aryloxy, such as phenoxy, 2-methylphenoxy, alpha- or beta-naphthyloxy, and 4-tolyloxy; carbonamido, such as acetamido, benzamido, butyramido, tetradecanamido, alpha-(2,4-di-t-pentylphenoxy)acetamido, alpha-(2,4-di-t-pentylphenoxy) butyramido, alpha-(3-pentadecylphenoxy)-hexanamido, a]pha-(4-hydroxy-3-t-butylphenoxy)tetradecanamido, 2-oxo-pyrrolidin-1-yl, 2-oxo-5-tetradecylpyrrolin-1-yl, N-methyltetradecanamido, N-succinimido, N-phthalimido, 2,5-dioxo-1 -oxazolidinyl, 3-dodecyl-2,5-dioxo-1-imidazolyl, and N-acetyl-N-dodecylamino, ethoxycarbonylamino, phenoxycarbonylamino, benzyloxycarbonylamino, hex adecyloxycarbonylamino, 2,4-di -t-butylphenoxycarbonylamino, phenylcarbonylamino, 2,5-(di -t-pentylphenyl)carbonyl amino, p-dodecylphenylcarbonyl amino, p-tolylcarbonyl amino, N-methylureido, N,N-dimethylureido, N-methyl-N-dodecylureido, N-hexadecylureido, N,N-dioctadecylureido, N,N-dioctyl-N'-ethylureido, N-phenylureido, N,N-diphenylureido, N-phenyl-N-p-tolylureido, N-(m-hexadecylphenyl)ureido, N,N-(2.5-di-t-pentylphenyl)-N'-ethylureido, and t-butylcarbonamido; sulfonamido, such as methylsulfonamido, benzenesulfonamido, p-tolylsulfonamido, p-dodecylbenzenesulfonamido, N-methyltetradecylsulfonamido, N,N-dipropylsulfamoylamino, and hexadecylsulfonamido; sulfamoyl, such as N-methylsulfamoyl, N-ethylsulfamoyl, N,N-dipropylsulfamoyl, N-hexadecylsulfamoyl, N,N-dimethylsultamoyl; N-[3-(dodecyloxy)propyl]sulfamoyl, N-[4-(2,4-di-t-pentylphenoxy)butyl]sulfamoyl, N-methyl-N-tetradecylsulfamoyl, and N-dodecylsulfamoyl; carbamoyl, such as N-methylcarbamoyl, N,N-dibutylcarbamoyl, N-octadecylcarbamoyl, N-[4-(2,4-di-t-pentylphenoxy)butyl]carbamoyl, N-methyl-N-tetradecylcarbamoyl, and N,N-dioctylcarbamoyl: acyl, such as acetyl, (2,4-di-t-amylphenoxy)acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl, and p-tolylsulfonyl; sulfonyloxy, such as dodecylsulfonyloxy, and hexadecylsulfonyloxy; sulfinyl, such as methylsulfinyl, octylsulfinyl, 2-ethylhexylsulfinyl, dodecylsulfinyl, hexadecylsulfinyl, phenylsulfinyl, 4-nonylphenylsulfinyl, and p-tolylsulfinyl; thio, such as ethylthio, octylthio, benzylthio, tetradecylthio, 2-(2,4-di-t-pentylphenoxy)ethylthio, phenylthio, 2-butoxy-5-t-octylphenylthio, and p-tolylthio; acyloxy, such as acetyloxy, benzoyloxy, octadecanoyloxy, p-dodecylamidobenzoyloxy, N-phenylcarbamoyloxy, N-ethylcarbamoyloxy, and cyclohexylcarbonyloxy; amine, such as phenylanilino, 2-chloroanilino, diethylamine, dodecylamine; imino, such as 1-(N-phenylimido)ethyl, N-succinimido or 3-benzylhydantoinyl; phosphate, such as dimethylphosphate and ethylbutylphosphate; phosphite, such as diethyl and dihexylphosphite; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen and sulfur, such as 2-furyl, 2-thienyl, 2-benzimidazolyloxy or 2-benzothiazolyl; quaternary ammonium, such as triethylammonium; and silyloxy, such as trimethylsilyloxy.

If desired, the substituents may themselves be further substituted one or more times with the described substituent groups. The particular substituents used may be selected by those skilled in the art to attain the desired photographic properties for a specific application and can include, for example, hydrophobic groups, solubilizing groups, blocking groups, releasing or releasable groups, etc. When a molecule may have two or more substituents, the substituents may be joined together to form a ring such as a fused ring unless otherwise provided. Generally, the above groups and substituents thereof may include those having up to 48 carbon atoms, typically 1 to 36 carbon atoms and usually less than 24 carbon atoms, but greater numbers are possible depending on the particular substituents selected.

The materials of the invention can be used in any of the ways and in any of the combinations known in the art. Typically, the invention materials are incorporated in a melt and coated as a layer described herein on a support to form part of a photographic element. When the term "associated" is employed, it signifies that a reactive compound is in or adjacent to a specified layer where, during processing, it is capable of reacting with other components.

To control the migration of various components, it may be desirable to include a high molecular weight hydrophobe or "ballast" group in coupler molecules. Representative ballast groups include substituted or unsubstituted alkyl or aryl groups containing 8 to 48 carbon atoms. Representative substituents on such groups include alkyl, aryl, alkoxy, aryloxy, alkylthio, hydroxy, halogen, alkoxycarbonyl, aryloxcarbonyl, carboxy, acyl, acyloxy, amino, anilino, carbonamido, carbamoyl, alkylsulfonyl, arylsulfonyl, to sulfonamido, and sulfamoyl groups wherein the substituents typically contain I to 42 carbon atoms. Such substituents can also be further substituted.

The photographic elements can be single color elements or multicolor elements. Multicolor elements contain image dye-forming units sensitive to each of the three primary regions of the spectrum. Each unit can comprise a single emulsion layer or multiple emulsion layers sensitive to a given region of the spectrum. The layers of the element, including the layers of the image-forming units, can be arranged in various orders as known in the art. In an alternative format, the emulsions sensitive to each of the three primary regions of the spectrum can be disposed as a single segmented layer.

A typical multicolor photographic element comprises a support bearing a cyan dye image-forming unit comprised of at least one red-sensitive silver halide emulsion layer having associated therewith at least one cyan dye-forming coupler, a magenta dye image-forming unit comprising at least one green-sensitive silver halide emulsion layer having associated therewith at least one magenta dye-forming coupler, and a yellow dye image-forming unit comprising at least one blue-sensitive silver halide emulsion layer having associated therewith at least one yellow dye-forming coupler. The element can contain additional layers, such as filter layers, interlayers, overcoat layers, subbing layers, and the like.

If desired, the photographic element can be used in conjunction with an applied magnetic layer as described in Research Disclosure, November 1992, Item 34390 published by Kenneth Mason Publications, Ltd., Dudley Annex, 12a North Street, Emsworth, Hampshire P010 7DQ, ENGLAND, and as described in Hatsumi Kyoukai Koukai Gihou No. 94-6023, published Mar. 15, 1994, available from the Japanese Patent Office, the contents of which are incorporated herein by reference. When it is desired to employ the inventive materials in a small format film, Research Disclosure, June 1994, Item 36230, provides suitable embodiments.

In the following discussion of suitable materials for use in the emulsions and elements of this invention, reference will be made to Research Disclosure, September 1996, Item 38957, available as described above, which is to referred to herein by the term "Research Disclosure". The contents of the Research Disclosure, including the patents and publications referenced therein, are incorporated herein by reference, and the Sections hereafter referred to are Sections of the Research Disclosure.

Except as provided, the silver halide emulsion containing elements employed in this invention can be either negative-working or positive-working as indicated by the type of processing instructions (i.e. color negative, reversal, or direct positive processing) provided with the element. Suitable emulsions and their preparation as well as methods of chemical and spectral sensitization are described in Sections I through V. Various additives such as UV dyes, brighteners, antifoggants, stabilizers, light absorbing and scattering materials, and physical property modifying addenda such as hardeners, coating aids, plasticizers, lubricants and matting agents are described, for example, in Sections II and VI through VIII. Color materials are described in Sections X through XIII Suitable methods for incorporating couplers and dyes, including dispersions in organic solvents, are described in Section X(E). Scan facilitating is described in Section XIV. Supports, exposure, development systems, and processing methods and agents are described in Sections XV to XX. The information contained in the September 1994 Research Disclosure, Item No. 36544 referenced above, is updated in the September 1996 Research Disclosure, Item No. 38957. Certain desirable photographic elements and processing steps, including those useful in conjunction with color reflective prints, are described in Research Disclosure, Item 37038, February 1995.

Coupling-off groups are well known in the art. Such groups can determine the chemical equivalency of a coupler, i.e., whether it is a 2-equivalent or a 4-equivalent coupler, or modify the reactivity of the coupler. Such groups can advantageously affect the layer in which the coupler is coated, or other layers in the photographic recording material, by performing, after release from the coupler, functions such as dye formation, dye hue adjustment, development acceleration or inhibition, bleach acceleration or inhibition, electron transfer facilitation, color correction and the like.

The presence of hydrogen at the coupling site provides a 4-equivalent coupler, and the presence of another coupling-off group usually provides a 2-equivalent coupler. Representative classes of such coupling-off groups include, for example, chloro, alkoxy, aryloxy, hetero-oxy, sulfonyloxy, acyloxy, acyl, heterocyclyl, sulfonamido, mercaptotetrazole, benzothiazole, mercaptopropionic acid, phosphonyloxy, arylthio, and arylazo. These coupling-off groups are described in the art, for example, in U.S. Pat. Nos. 2,455, 169, 3,227,551, 3,432,521, 3,476,563, 3,617,291, 3,880,661, 4,052,212 and 4,134,766; and in UK. Patents and published application Nos. 1,466,728, 1,531,927, 1,533,039, 2,006, 755A and 2,017,704A, the disclosures of which are incorporated herein by reference.

Image dye-forming couplers may be included in the element such as couplers that form cyan dyes upon reaction with oxidized color developing agents which are described in such representative patents and publications as: "Farbkuppler-eine Literature Ubersicht," published in Agfa Mitteilungen, Band III, pp. 156–175 (1961) as well as in U.S. Pat. Nos. 2,367,531; 2,423,730; 2,474,293; 2,772,162; 2,895,826; 3,002,836; 3,034,892; 3,041,236; 4,333,999; 4,746,602; 4,753,871; 4,770,988; 4,775,616; 4,818,667; 4,818,672; 4,822,729; 4,839,267; 4,840,883; 4,849,328; 4,865,961; 4,873,183; 4,883,746; 4,900,656; 4,904,575; 4,916,051; 4,921,783; 4,923,791; 4,950,585; 4,971,898; 4,990,436; 4,996,139; 5,008,180; 5,015,565; 5,011,765; 5,011,766; 5,017,467; 5,045,442; 5,051,347; 5,061,613; 5,071,737; 5,075,207; 5,091,297; 5,094,938; 5,104,783; 5,178,993; 5,813,729; 5,187,057; 5,192,651; 5,200,305 5,202,224; 5,206,130; 5,208,141; 5,210,011; 5,215,871; 5,223,386; 5,227,287; 5,256,526; 5,258,270; 5,272,051; 5,306,610; 5,326,682; 5,366,856; 5,378,596; 5,380,638; 5,382,502; 5,384,236; 5,397,691; 5,415,990; 5,434,034; 5,441,863; EPO 0 246 616; EPO 0 250 201; EPO 0 271 323; EPO 0 295 632; EPO 0 307 927; EPO 0 333 185; EPO 0 378 898;EPO 0 389 817; EPO 0 487 111; EPO 0 488 248; EPO 0 539 034; EPO 0 545 300; EPO 0 556 700; EPO 0 556 777; EPO 0 556 858; EPO 0 569 979; EPO 0 608 133; EPO 0 636 936; EPO 0 651 286; EPO 0 690 344; German OLS 4,026,903; German OLS 3,624,777. and German OLS 3,823,049. Typically such couplers are phenols, naphthols, or pyrazoloazoles.

Couplers that form magenta dyes upon reaction with oxidized color developing agent are described in such representative patents and publications as: "Farbkuppler-eine Literature Ubersicht," published in Agfa Mitteilungen, Band III, pp. 126–156(1961) as well as U.S. Pat. Nos. 2,311,082 and 2,369,489; 2,343,701; 2,600,788; 2,908,573; 3,062,653; 3,152,896; 3,519,429; 3,758,309; 3,935,015; 4,540,654; 4,745,052; 4,762,775; 4,791,052; 4,812,576; 4,835,094; 4,840,877; 4,845,022; 4,853,319; 4,868,099; 4,865,960; 4,871,652; 4,876,182; 4,892,805; 4,900,657; 4,910,124; 4,914,013; 4,921,968; 4,929,540; 4,933,465; 4,942,116; 4,942,117; 4,942,118; U.S. Pat. Nos. 4,959,480; 4,968,594; 4,988,614; 4,992,361; 5,002,864; 5.021,325; 5,066,575; 5,068,171; 5,071,739; 5,100,772; 5,110,942; 5,116,990; 5,118,812; 5,134,059; 5,155,016; 5,183,728; 5,234,805; 5,235,058; 5,250,400; 5,254,446; 5,262,292; 5,300,407; 5,302,496; 5,336,593; 5,350,667; 5,395,968; 5,354,826; 5,358,829; 5,368,998; 5,378,589; 5,409,808; 5,411,841; 5,418,123; 5,424,179; EPO 0 257 854; EPO 0 284 240; EPO 0 341 204; EPO 0 347,235; EPO 0 365,252; EPO 0 422 595; EPO 0 428 899; EPO 0 428 902; EPO 0 459 331; EPO 0 467 327; EPO 0 476 949; EPO 0 487 081; EPO 0489 333; EPO 0 512 304;EPO 0 515 128;EPO 0 534 703;EPO 0 554 778;EPO 0 558 145; EPO 0 571 959; EPO 0 583 832; EPO 0 583 834; EPO 0 584 793; EPO 0 602 748; EPO 0 602 749; EPO 0 605 918; EPO 0 622 672; EPO 0 622 673; EPO 0 629 912; EPO 0 646 841, EPO 0 656 561; EPO 0 660 177; EPO 0 686 872; WO 90/10253; WO 92/09010; WO 92/10788; WO 92/12464; WO 93/01523; WO 93/02392; WO 93/02393; WO 93/07534; UK Application 2,244,053; Japanese Application 03192-350; German OLS 3,624,103; German OLS 3,912,265; and German OLS 4,008,067. Typically such couplers are pyrazolones, pyrazoloazoles, or pyrazolobenzimidazoles that form magenta dyes upon reaction with oxidized color developing agents.

Couplers that form yellow dyes upon reaction with oxidized color developing agent are described in such representative patents and publications as:

"Farbkuppler-eine Literature Ubersicht," published in Agfa Mitteilungen; Band III; to pp. 112–126 (1961); as well as U.S. Pat. Nos. 2,298,443; 2,407,210; 2,875,057; 3,048, 194; 3,265,506; 3,447,928; 4,022,620; 4,443,536; 4,758, 501; 4,791,050; 4,824,771; 4,824,773; 4,855,222; 4,978, 605; 4,992,360; 4,994,361; 5,021,333; 5,053,325; 5,066, 574; 5,066,576; 5,100,773; 5,118,599; 5,143,823; 5,187, 055; 5,190,848; 5,213,958; 5,215,877; 5,215,878; 5,217, 857; 5,219,716; 5,238,803; 5,283,166; 5,294,531; 5,306, 609; 5,328,818; 5,336,591; 5,338,654; 5,358,835; 5,358, 838; 5,360,713; 5,362,617; 5,382,506; 5,389,504; 5,399, 474;. 5,405,737; 5,411,848; 5,427,898; EPO 0 327 976; EPO 0 296 793; EPO 0 365 282; EPO 0 379 309; EPO 0 415 375; EPO 0 437 818; EPO 0 447 969; EPO 0 542 463; EPO 0 568 037; EPO 0 568 196; EPO 0 568 777; EPO 0 570 006; EPO 0 573 761; EPO 0 608 956; EPO 0 608 957; and EPO 0 628 865. Such couplers are typically open chain ketomethylene compounds.

Couplers that form colorless products upon reaction with oxidized color developing agent are described in such representative patents as:

UK. 861,138; U.S. Pat. Nos. 3,632,345; 3,928,041; 3,958, 993 and 3,961,959. Typically such couplers are cyclic carbonyl containing compounds that form colorless products on reaction with an oxidized color developing agent.

Couplers that form black dyes upon reaction with oxidized color developing agent are described in such representative patents as U.S. Pat. Nos. 1,939,231; 2,181,944; 2,333,106; and 4,126,461; German OLS No. 2,644,194 and German OLS No. 2,650,764. Typically, such couplers are resorcinols or m-aminophenols that form black or neutral products on reaction with oxidized color developing agent.

In addition to the foregoing, so-called "universal" or "washout" couplers may be employed. These couplers do not contribute to image dye-formation. Thus, for example, a naphthol having an unsubstituted carbamoyl or one substituted with a low molecular weight substituent at the 2- or 3-position may be employed. Couplers of this type are described, for example, in U.S. Pat. Nos. 5,026,628, 5,151, 343, and 5,234,800.

It may be useful to use a combination of couplers any of which may contain known ballasts or coupling-off groups such as those described in U.S. Pat. No. 4,301,235; U.S. Pat. No. 4,853,319 and U.S. Pat. No. 4,351,897. The coupler may contain solubilizing groups such as described in U.S. Pat. No. 4,482,629. The coupler may also be used in association with "wrong" colored couplers (e.g. to adjust levels of interlayer correction) and, in color negative applications, with 1 masking couplers such as those described in EP 213.490; Japanese Published Application 58-172,647; U.S. Pat. Nos. 2,983,608; 4,070,191; and 4,273,861; German Applications DE 2,706,117 and DE 2,643,965; UK. Patent 1,530,272; and Japanese Application 58-113935. The masking couplers may be shifted or blocked, if desired.

Typically, couplers are incorporated in a silver halide emulsion layer in a mole ratio to silver of 0.05 to 1.0 and generally 0.1 to 0.5. Useful coated levels of the DIR couplers of this invention range from about 0.005 to 0.50 g/m$^2$ or more, typically form 0.01 to 0.30 g/m$^2$. The couplers of this invention are usually utilized by dissolving them in high-boiling coupler solvents and then dispersing the organic coupler plus coupler solvent mixtures as small particles in aqueous solutions of gelatin and surfactant (via milling or homogenization). Removable auxiliary organic solvents such as ethyl acetate or cyclohexanone may also be used in the preparation of such dispersions to facilitate the dissolution of the coupler in the organic phase. Coupler solvents useful for the practice of this invention include aryl phosphates (e.g. tritolyl phosphate), alkyl phosphates (e.g. trioctyl phosphate), mixed aryl alkyl phosphates (e.g. diphenyl 2-ethylhexyl phosphate), aryl, alkyl or mixed aryl-alkyl phosphonates, phosphine oxides (e.g. trioctylphosphine oxide), esters of aromatic acids (e.g. dibutyl phthalate, octyl benzoate, or benzyl salicylate), esters of aliphatic acids (e.g. acetyl tributyl citrate, tripentyl citrate, or dibutyl sebacate), alcohols (e.g. 2-hexyl-1-decanol), phenols (e.g. p-docecylphenol), carbonamides(e.g. N,N-dibutyldodecanamide or N-butylacetanilide), sulfoxides (e.g. bis(2-ethylhexyl)sulfoxide), sulfonamides (e.g. N,N-dibutyl-p-toluenesulfonamide) or hydrocarbons (e.g. dodecylbenzene). Additional coupler solvents and auxiliary solvents are noted in Research Disclosure, December 1989, Item 308119, p. 993. Useful coupler: coupler solvent weight ratios range from about 1:0.1 to 1:8.0 with 1:0.2 to 1:4.0 being preferred. Dispersions using no permanent coupler solvent are sometimes employed.

The invention materials may be used in association with materials that release Photographically Useful Groups (PUGS) that accelerate or otherwise modify the processing steps e.g. of bleaching or fixing to improve the quality of the image. Bleach accelerator releasing couplers such as those described in EP 193,389; EP 301,477; U.S. Pat. No. 4,163, 669; U.S. Pat. No. 4,865,956; and U.S. Pat. No. 4,923,784, may be useful. Also contemplated is use of the compositions in association with nucleating agents, development accelerators or their precursors (UK Patent 2,097,140; UK. Patent 2,131,188); electron transfer agents (U.S. Pat. No. 4,859, 578; U.S. Pat. No. 4,912,025); antifogging and anti color-mixing agents such as derivatives of hydroquinones, aminophenols, amines, gallic acid; catechol; ascorbic acid; hydrazides; sulfonamidophenols; and non color-forming couplers.

The invention materials may also be used in combination with filter dye layers comprising colloidal silver sol or yellow, cyan, and/or magenta filter dyes, either as oil-in-water dispersions, latex dispersions or as solid particle dispersions. Additionally, they may be used with "smearing" couplers (e.g. as described in U.S. Pat. No. 4,366,237; EP 96,570; U.S. Pat. No. 4,420,556; and U.S. Pat. No. 4,543, 323.) Also, the compositions may be blocked or coated in protected form as described, 30 for example, in Japanese Application 61/258,249 or U.S. Pat. No. 5,019,492.

The invention materials may further be used in combination with image-modifying compounds that release PUGS such as "Developer Inhibitor-Releasing" compounds (DIR's). DIR's useful in conjunction with the compositions of the invention are known in the art and examples are described in U.S. Pat. Nos. 3,137,578; 3,148,022; 3,148, 062; 3,227,554; 3,384,657; 3,379,529; 3,615,506; 3,617, 291; 3,620,746; 3,701,783; 3,733,201; 4,049,455; 4,095, 984; 4,120,459; 4,149,886; 4,150,228; 4,211,562; 4,248, 962; 4,259,437; 4,362,878; 4,409,323; 4,477,563; 4,782,012; 4,962,018; 4,500,634; 4,579,816; 4,607,004; 4,618,571; 4,678,739; 4,746,600; 4,746,601; 4,791,049; 4,857,447; 4,865,959; 4,880,342; 4,886,736; 4,937,179; 4,946,767; 4,948,716; 4,952,485; 4,956,269; 4,959,299; 4,966,835; 4,985,336 as well as in patent publications GB 1,560,240; GB 2,007,662; GB 2,032,914; GB 2,099,167; DE 2,842,063, DE 2,937,127; DE 3,636,824; DE 3,644,416 as well as the following European Patent Publications: 272,573; 335,319; 336,411; 346, 899; 362, 870; 365,252; 365, 346; 373,382; 376,212; 377,463; 378,236; 384,670; 396, 486; 401,612; 401,613.

Such compounds are also disclosed in "Developer-Inhibitor-Releasing (DIR) Couplers for Color Photography," C. R. Barr, J. R. Thirtle and P. W. Vittum in *Photographic Science and Engineering*, Vol. 13, p. 174 (1969), incorporated herein by reference. Generally, the developer inhibitor-releasing (DIR) couplers include a coupler moiety and an inhibitor coupling-off moiety (IN). The inhibitor-releasing couplers may be of the time-delayed type (DIAR couplers) which also include a timing moiety or chemical switch which produces a delayed release of inhibitor. Examples of typical inhibitor moieties are: oxazoles, thiazoles, diazoles, triazoles, oxadiazoles, thiadiazoles, oxathiazoles, thiatriazoles, benzotriazoles, tetrazoles, benzimidazoles, indazoles, isoindazoles, mercaptotetrazoles, selenotetrazoles, mercaptobenzothiazoles, selenobenzothiazoles, mercaptobenzoxazoles, selenobenzoxazoles, mercaptobenzi midazoles, selenobenzimidazoles, benzodi azoles, mercaptooxazoles, mercaptothiadiazoles, mercaptothiazoles, mercaptotriazoles, mercaptooxadi azoles, mercaptodiazoles, mercaptooxathi azoles, tellurotetrazoles or benzisodiazoles. In a preferred embodiment, the inhibitor moiety or group is selected from the following formulas:

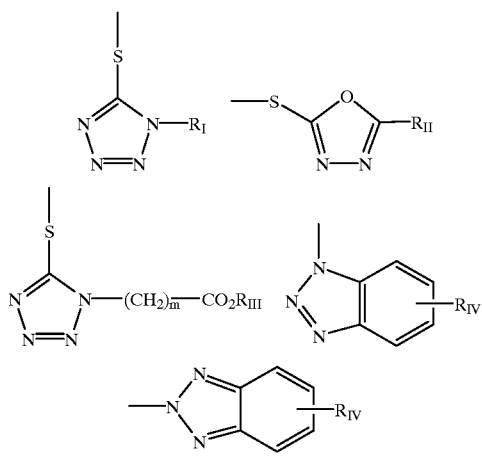

wherein $R_I$ is selected from the group consisting of straight and branched alkyls of from 1 to about 8 carbon atoms, benzyl, phenyl, and alkoxy groups and such groups containing none, one or more than one such substituent; $R_{II}$ is selected from $R_I$ and —$SR_I$; $R_{III}$ is a straight or branched alkyl group of from 1 to about 5 carbon atoms and m is from 1 to 3; and $R_{IV}$ is selected from the group consisting of hydrogen, halogens and alkoxy, phenyl and carbonamido groups, —$COOR_V$ and —$NHCOOR_V$ wherein $R_V$ is selected from substituted and unsubstituted alkyl and aryl groups.

Although it is typical that the coupler moiety included in the developer inhibitor-releasing coupler forms an image dye corresponding to the layer in which it is located, it may also form a different color as one associated with a different film layer. It may also be useful that the coupler moiety included in the developer inhibitor-releasing coupler forms colorless products and/or products that wash out of the photographic material during processing (so-called "universal" couplers).

A compound such as a coupler may release a PUG directly upon reaction of the compound during processing, or indirectly through a timing or linking group. A timing group produces the time-delayed release of the PUG such groups using an intramolecular nucleophilic substitution reaction (U.S. Pat. No. 4,248,962); groups utilizing an electron transfer reaction along a conjugated system (U.S. Pat. Nos. 4,409,323; 4,421,845; 4,861,701, Japanese Applications 57-188035; 58-98728; 58-209736; 58-209738); groups that function as a coupler or reducing agent after the coupler reaction (U.S. Pat. No. 4,438,193; U.S. Pat. No. 4,618,571) and groups that combine the features describe above. It is typical that the timing group is of one of the formulas:

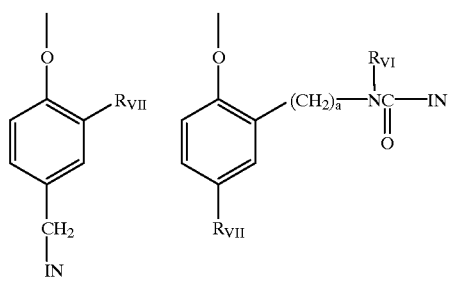

wherein IN is the inhibitor moiety, $R_{VII}$ is selected from the group consisting of nitro, cyano, alkylsulfonyl; sulfamoyl; and sulfonamido groups; a is 0 or 1; and $R_{VI}$ is selected from the group consisting of substituted and unsubstituted alkyl and phenyl groups. The oxygen atom of each timing group is bonded to the coupling-off position of the respective coupler moiety of the DIAR.

The timing or linking groups may also function by electron transfer down an unconjugated chain. Linking groups are known in the art under various names. Often they have been referred to as groups capable of utilizing a hemiacetal or iminoketal cleavage reaction or as groups capable of utilizing a cleavage reaction due to ester hydrolysis such as U.S. Pat. No. 4,546,073. This electron transfer down an unconjugated chain typically results in a relatively fast decomposition and the production of carbon dioxide, formaldehyde, or other low molecular weight by-products. The groups are exemplified in EP 464,612, EP 523,45 1, U.S. Pat. No. 4,146,396, Japanese Kokai 60-249148 and 60-249149.

Suitable developer inhibitor-releasing couplers for use in the present invention include, but are not limited to, the following:

D1
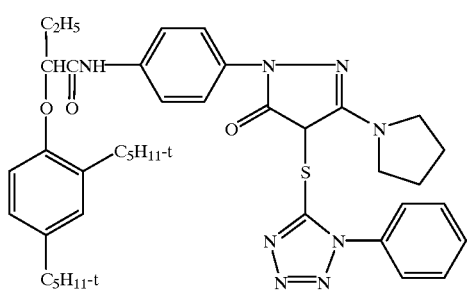
D2
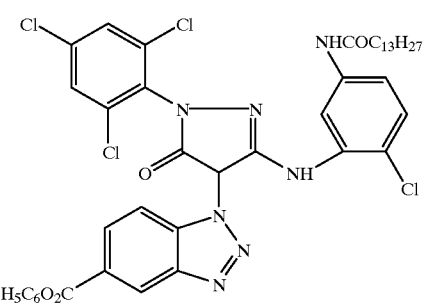
D3
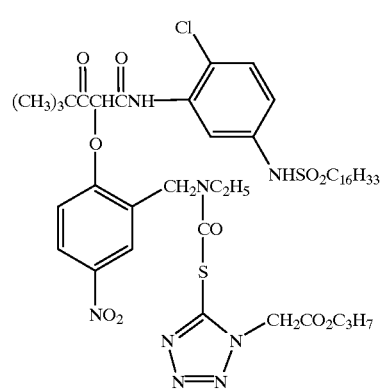
D4
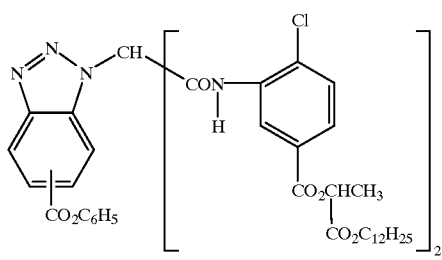
D5
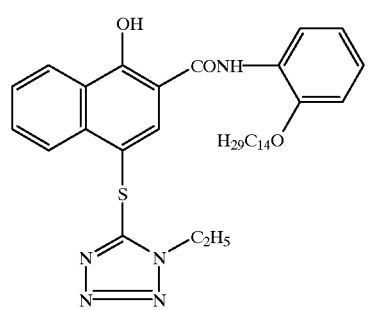
-continued
D6
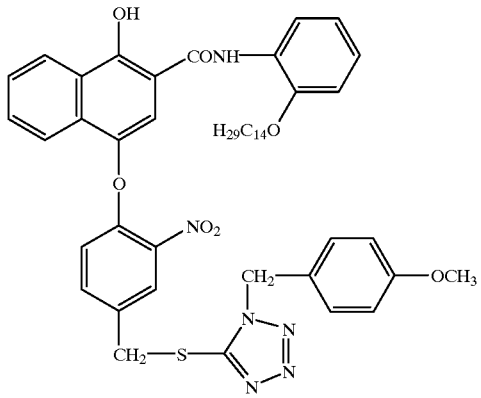
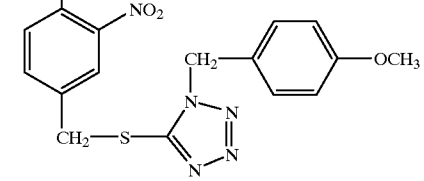
D7
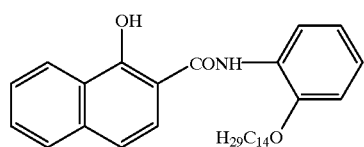
D8
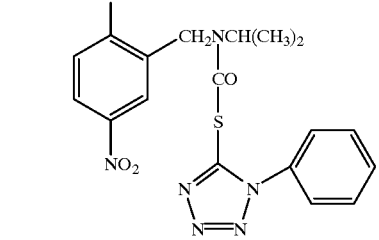

D9
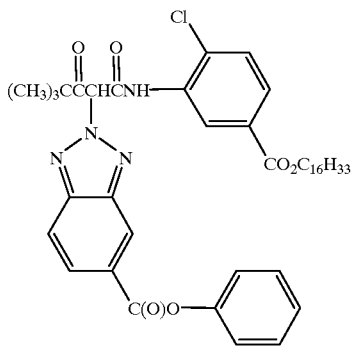

D10
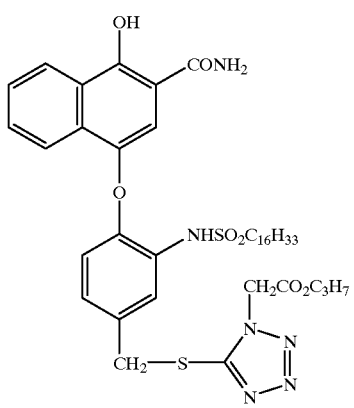

D11
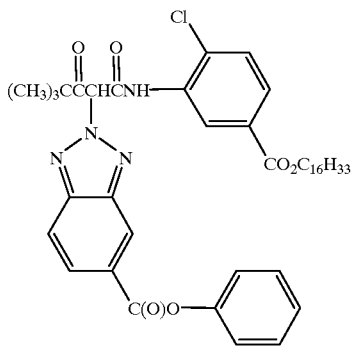

D12
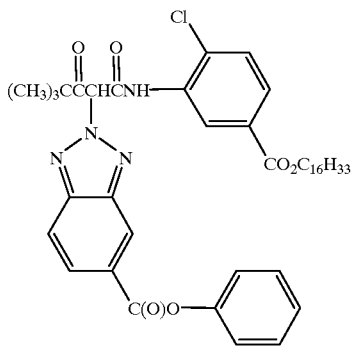

It is also contemplated that the concepts of the present invention may be employed to obtain reflection color prints as described in *Research Disclosure,* November 1979, Item 18716, available from Kenneth Mason Publications, Ltd, Dudley Annex, 12a North Street, Emsworth, Hampshire P0101 7DQ, England, incorporated herein by reference. Materials of the invention may be coated on pH adjusted support as described in U.S. Pat. No. 4,917,994; on a support with reduced oxygen permeability (EP 553,339); with epoxy solvents (EP 164,961); with nickel complex stabilizers (U.S. Pat. No. 4,346,165; U.S. Pat. No. 4,540,653 and U.S. Pat. No. 4,906,559 for example); with ballasted chelating agents such as those in U.S. Pat. No. 4,994,359 to reduce sensitivity to polyvalent cations such as calcium; and with stain reducing compounds such as described in U.S. Pat. No. 5,068,171. Other compounds useful in combination with the invention are disclosed in Japanese Published Applications described in Derwent Abstracts having accession numbers as follows: 90-072,629; 90-072,630; 90-072,631; 90-072,632; 90-072,633; 90-072,634; 90-077,822; 90-078,229; 90-078,230; 90-079,336; 90-079,337; 90-079,338; 90-079,690; 90-079,691; 90-080,487; 90-080,488; 90-080,489; 90-080,490; 90-080,491; 90-080,492; 90-080,494; 90-085,928; 90-086,669; 90-086,670; 90-087,360; 90-087,361; 90-087,362; 90-087,363; 90-087,364; 90-088,097; 90-093,662; 90-093,663; 90-093,664; 90-093,665; 90-093,666; 90-093,668; 90-094,055; 90-094,056; 90-103,409; 83-62,586; 83-09,959.

Conventional radiation-sensitive silver halide emulsions can be employed in the practice of this invention. Such emulsions are illustrated by *Research Disclosure,* Item 38755, September 1996, I. Emulsion grains and their preparation.

Especially useful in this invention are tabular grain silver halide emulsions. Tabular grains are those having two parallel major crystal faces and having an aspect ratio of at least 2. The term "aspect ratio" is the ratio of the equivalent circular diameter (ECD) of a grain major face divided by its thickness (t). Tabular grain emulsions are those in which the tabular grains account for at least 50 percent (preferably at least 70 percent and optimally at least 90 percent) of the total grain projected area. Preferred tabular grain emulsions are those in which the average thickness of the tabular grains is less than 0.3 micrometer (preferably thin—that is, less than 0.2 micrometer and most preferably ultrathin—that is, less than 0.07 micrometer). The major faces of the tabular grains can lie in either {111 } or {100} crystal planes. The mean ECD of tabular grain emulsions rarely exceeds 10 micrometers and more typically is less than 5 micrometers.

In their most widely used form tabular grain emulsions are high bromide {111 } tabular grain emulsions. Such emulsions are illustrated by Kofron et al U.S. Pat. No. 4,439,520, Wilgus et al U.S. Pat. No. 4,434,226, Solberg et al U.S. Pat. No. 4,433,048, Maskasky U.S. Pat. Nos. 4,435, 501, 4,463,087 and 4,173,320, Daubendiek et al U.S. Pat. Nos. 4,414,310 and 4,914,014, Sowinski et al U.S. Pat. No. 4,656,122, Piggin et al U.S. Pat. Nos. 5,061,616 and 5,061, 609, Tsaur et al U.S. Pat. Nos. 5.147,771, '772, '773, 5,171,659 and 5,252,453, Black et al U.S. Pat. Nos. 5,219, 720 and 5,334,495, Delton U.S. Pat. Nos. 5,310,644, 5,372, 927 and 5,460,934, Wen U.S. Pat. No. 5,470,698, Fenton et al U.S. Pat. No. 5,476,760, Eshelman et al U.S. Pat. Nos. 5,612,,175 and 5,614,359, and Irving et al U.S. Pat. No. 5,667,954.

Ultrathin high bromide {111 } tabular grain emulsions are illustrated by Daubendick et al U.S. Pat. Nos. 4,672,027, 4,693,964, 5,494,789, 5,503,971 and 5,576,168, Antoniades et al U.S. Pat. No. 5,250,403, Olm et al U.S. Patent 5,503, 970, Deaton et al U.S. Pat. No. 5,582,965, and Maskasky U.S. Pat. No. 5,667,955.

High bromide {100} tabular grain emulsions are illustrated by Mignot U.S. Pat. Nos. 4,386,156 and 5,386,156.

High chloride {111 } tabular grain emulsions are illustrated by Wey U.S. Pat. No. 4,399,215, Wey et al U.S. Pat. No. 4,414,306, Maskasky U.S. Pat. Nos. 4,400,463, 4,713, 323, 5,061,617, 5,178,997, 5,183,732, 5,185,239, 5,399,478 and 5,411,852, and Maskasky et al U.S. Pat. Nos. 5,176,992 and 5,178,998. Ultrathin high chloride {111 } tabular grain emulsions are illustrated by Maskasky U.S. Pat. Nos. 5,271, 858 and 5,389,509.

High chloride {100} tabular grain emulsions are illustrated by Maskasky U.S. Pat. Nos. 5,264,337, 5,292,632, 5,275,930 and 5,399,477, House et al U.S. Pat. No. 5,320, 938, Brust et al U.S. Pat. No. 5,314,798, Szajewski et al U.S. Pat. No. 5,356,764, Chang et al U.S. Pat. Nos. 5,413,904 and 5,663,041, Oyamada U.S. Pat. No. 5,593,82 1, Yamashita et al U.S. Pat. Nos. 5,641,620 and 5,652,088, Saitou et al U.S. Pat. No. 5,652,089, and Oyamada et al U.S. Pat. No. 5,665,530. Ultrathin high chloride {100} tabular grain emulsions can be prepared by nucleation in the presence of iodide, following the teaching of House et al and Chang et al, cited above.

The emulsions can be surface-sensitive emulsions, i.e., emulsions that form latent images primarily on the surfaces of the silver halide grains, or the emulsions can form internal latent images predominantly in the interior of the silver halide grains. The emulsions can be negative-working emulsions, such as surface-sensitive emulsions or unfogged internal latent image-forming emulsions, or direct-positive emulsions of the unfogged, internal latent image-forming type, which are positive-working when development is conducted with uniform light exposure or in the presence of a nucleating agent. Tabular grain emulsions of the latter type are illustrated by Evans et al. U.S. Pat. No. 4,504,570.

Photographic elements can be exposed to actinic radiation, typically in the visible region of the spectrum, to form a latent image and can then be processed to form a visible dye image. Processing to form a visible dye image includes the step of contacting the element with a color developing agent to reduce developable silver halide and oxidize the color developing agent. Oxidized color developing agent in turn reacts with the coupler to yield a dye. If desired "Redox Amplification" as described in Research Disclosure XVIIIB(5) may be used.

With negative-working silver halide, the processing step described above provides a negative image. One type of such element, referred to as a color negative film, is designed for image capture. Speed (the sensitivity of the element to low light conditions) is usually critical to obtaining sufficient image in such elements. Such elements are typically silver bromoiodide emulsions coated on a transparent support and are sold packaged with instructions to process in known color negative processes such as the Kodak C-41 process as described in The British Journal of Photography Annual of 1988, pages 191–198. If a color negative film element is to be subsequently employed to generate a viewable projection print as for a motion picture, a process such as the Kodak ECN-2 process described in the H-24 Manual available from Eastman Kodak Co. may be employed to provide the color negative image on a transparent support. Color negative development times are typically 3' 15" or less and desirably 90 or even 60 seconds or less.

The photographic element of the invention can be incorporated into exposure structures intended for repeated use or exposure structures intended for limited use, variously referred to by names such as "single use cameras", "lens with film", or "photosensitive material package units".

Another type of color negative element is a color print. Such an element is designed to receive an image optically printed from an image capture color negative element. A color print element may be provided on a reflective support for reflective viewing (e.g. a snap shot) or on a transparent support for projection viewing as in a motion picture. Elements destined for color reflection prints are provided on a reflective support, typically paper, employ silver chloride emulsions, and may be optically printed using the so-called negative-positive process where the element is exposed to light through a color negative film which has been processed as described above. The element is sold packaged with instructions to process using a color negative optical printing process, for example the Kodak RA-4 process, as generally described in PCT WO 87/04534 or U.S. Pat. No. 4,975,357, to form a positive image. Color projection prints may be processed, for example, in accordance with the Kodak ECP-2 process as described in the H-24 Manual. Color print development times are typically 90 seconds or less and desirably 45 or even 30 seconds or less.

A reversal element is capable of forming a positive image without optical printing. To provide a positive (or reversal) image, the color development step is preceded by development with a non-chromogenic developing agent to develop exposed silver halide, but not form dye, and followed by uniformly fogging the element to render unexposed silver halide developable. Such reversal elements are typically sold packaged with instructions to process using a color reversal process such as the Kodak E-6 process as described in The British Journal of Photography Annual of 1988, page 194. Alternatively, a direct positive emulsion can be employed to obtain a positive image.

The above elements are typically sold with instructions to process using the appropriate method such as the mentioned color negative (Kodak C-41), color print (Kodak RA-4), or reversal (Kodak E-6) process.

Preferred color developing agents are p-phenylenediamines such as:

4-amino-N,N-diethylaniline hydrochloride,
4-amino-3-methyl-N,N-diethylaniline hydrochloride,
4-amino-3-methyl-N-ethyl-N-(2-methanesulfonamidoethyl)aniline sesquisulfate hydrate,
4-amino-3-methyl-N-ethyl-N-(2-hydroxyethyl)aniline sulfate,
4-amino-3-(2-methanesulfonamidoethyl)-N,N-diethylaniline hydrochloride, and
4-amino-N-ethyl-N-(2-methoxyethyl)-m-toluidine di-p-toluene sulfonic acid.

Development is usually followed by the conventional steps of bleaching, fixing, or bleach-fixing, to remove silver or silver halide, washing, and drying.

Synthesis

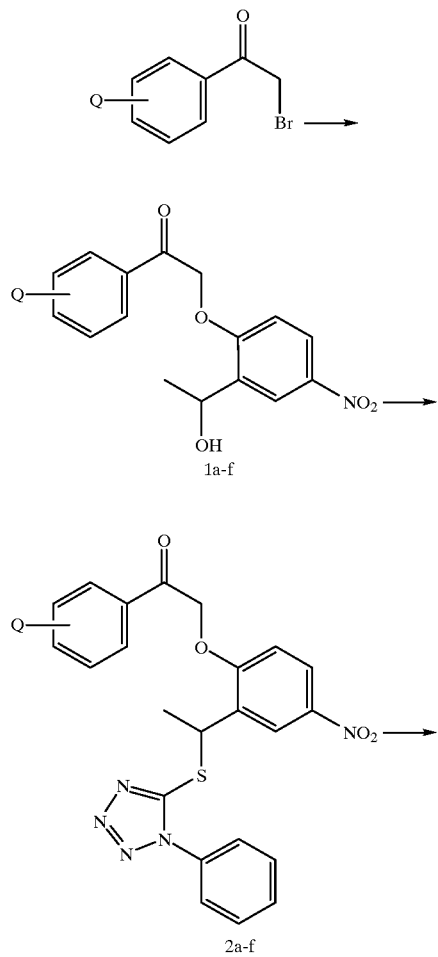

Scheme 1.

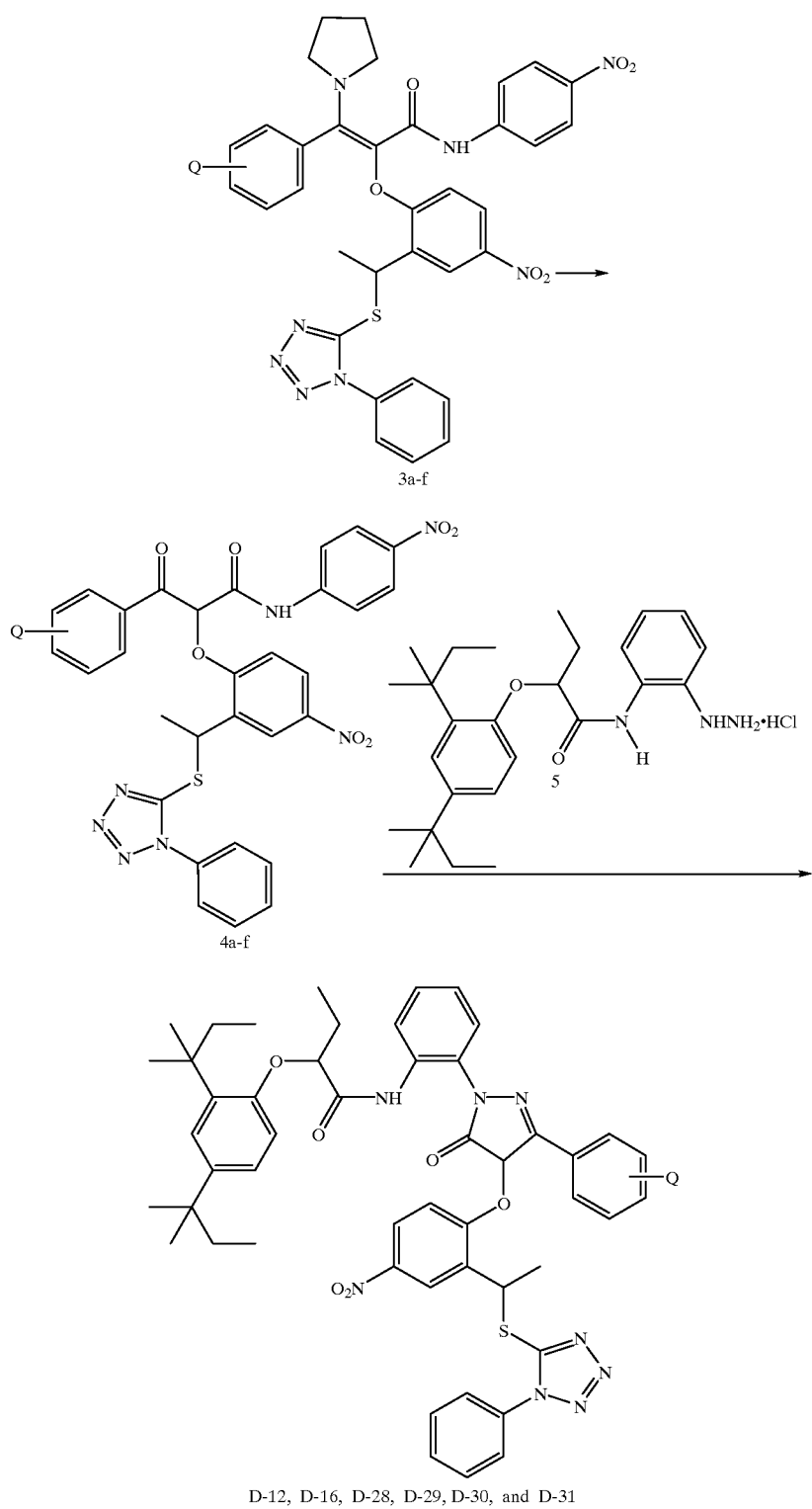
| 1–4 | Coupler | Q |
|---|---|---|
| a | D-12 | 3,4-di Cl |
| b | D-16 | 4-Cl |
| c | D-28 | 3-OCH₃ |
| d | D-29 | 4-OCH₃ |

-continued

| | | |
|---|---|---|
| e | D-30 | 4-F |
| f | D-31 | H |

Coupler D-16.
Preparation of 1b.

A mixture of 2-bromo-4'-chloroacetophenone (23.35 g, 100 mmol), 1-(2-hydroxy-5-nitrophenyl)ethanol (18.50 g, 101 mmol), and potassium carbonate (14.10 g, 102 mmol) in N,N-dimethylformamide (150 mL) was stirred at room temperature for 3 hours. The mixture was then poured into 1200 mL of water, the precipitated solid collected, washed with water (5×300 mL), ethanol (2×75 mL) and dried in vacuo for 16 hours. The yield of 1b was 31.04 g (92 mmol, 92%).

Preparation of 2b.

Boron trifluoride etherate (ca. 50%, 2.90 g, 10 mmol) was added to a suspension of 1b (33.57 g, 100 mmol) and 1-phenyl-5-mercaptotetrazole (18.71 g, 105 mmol) in 200 mL of 1,2-dichloroethane. The mixture was refluxed for 20 min using a water trap to collect ca. 1.5 mL of water. The solvent was distilled off and the residue recrystallized form ethanol (150 mL) to give 31.41 g (63 mmol, 63%) of 2b.

Preparation of 3b.

A solution of pyrrolidine (20 mL, 288 mmol) and 2b (39.68 g, 80 mmol) in 200 mL of toluene was refluxed for 2 h using a Dean-Stark trap to collect ca. 1.1 mL of water. The solvent and excess pyrrolidine were distilled off. The residue was dissolved in 200 mL of toluene, 4-nitrophenyl isocyanate (13.13 g, 80 mmol) was added, the mixture refluxed for 30 min, stirred at room temperature for 24 h and filtered. The solid product was washed with toluene (200 mL) and dried to produce 48.06 g of 3b (67 mmol, 84%).

Preparation of 4b.

Concentrated hydrochloric acid (6 mL) was added to a slurry of 3b (42.79 g, 60 mmol) in 300 mL of ethanol and the mixture was refluxed for 6 h, stirred at room temperature for 2 h and filtered. The collected solid was washed with ethanol (2×50 mL) and dried giving 35.03 g (53 mmol, 88%) of 4b.

Preparation of D-16.

Solid 5 (18.48 g, 40 mmol) was added in portions over a period of 2 h to a refluxing solution of 4b (16.50 g, 25 mmol) in 200 mL of acetic acid/400 mL of ethyl acetate. Following the addition, the mixture was refluxed for 1.5 h, cooled to room temperature and worked up with more ethyl acetate and 5% aqueous hydrochloric acid. The crude product was purified by column chromatography and finally recrystallized from isopropyl ether to give 12.92 g of D-16 (14 mmol, 56%), m.p. 179–180° C., $M^+$ 929.

Coupler D-28.
Preparation of 1c.

Prepared from 3'-methoxy-2-bromoacetophenone (22.91 g, 100 mmol) and 1-(2-hydroxy-5-nitrophenyl)ethanol (18.50 g, 101 mmol) as described for 1b. The yield of 1c was 31.40 g (95 mmol, 95%).

Preparation of 2c.

Prepared from 1c (29.82 g, 90 mmol) and 1-phenyl-5-mercaptotetrazole (16.57 g, 93 mmol) as described for 2b. The yield of 2c was 17.95 g (37 mmol, 41%).

Preparation of 3c and 4c.

Compound 3c was prepared as described for 3b, beginning with 17.20 g (35 mmol) of 2c. The crude enamine 3c was then hydrolyzed with conc. HCl in ethanol to give 17.77 g (27 mmol, 77%) of 4c.

Preparation of D-28.

A mixture of 4c (16.39 g, 25 mmol) and 5 (18.48 g, 40 mmol) in 250 mL of acetic acid was refluxed for 45 min giving a clear solution. The reaction mixture was cooled to room temperature, poured into 1200 mL of water, and extracted with 3×300 mL of ether. The extracts were dried over magnesium sulfate and concentrated in vacuo to a foam which was purified by column chromatography on silica gel. The crude product was recrystallized from isopropyl ether/heptanes (1:1) giving 5.95 g (6.4 mmol, 26%) of D-28, m.p. 158–159° C., $M^+$ 925.

Coupler D-30.
Preparation of 1e.

Prepared from 4'-fluoro-2-bromoacetophenone (100 mmol) and 1-(2-hydroxy-5-nitrophenyl)ethanol (18.50 g, 101 mmol) as described for 1b. The yield of 1e was 21.75 g (68 mmol, 68%).

Preparation of 2e.

Prepared from 1e (21.07 g, 66 mmol) and 1-phenyl-5-mercaptotetrazole (12.30 g, 69 mmol) as described for 2b. The yield of 2e was 20.04 g (42 mmol, 63%).

Preparation of 3e and 4e.

Compound 3e was prepared as described for 3b, beginning with 19.18 g (40 mmol) of 2e. The crude enamine 3e was then hydrolyzed with conc. HCl in refluxing ethanol to give 14.96 g (23 mmol, 58%) of 4e.

Preparation of D-30.

Solid ballasted phenylhydrazine hydrochloride (5, 9.24 g, 20 mmol) was added in portions over a period of 2 h to a refluxing solution of 4e (12.87 g, 20 mmol) in 150 mL of propyl acetate. Following the addition the solution was refluxed for 1 h, cooled to room temperature and worked up with water and more propyl acetate. The crude product was purified by column chromatography and recrystallization from isopropyl ether. The yield of D-30 was 4.71 g (5 mmol, 26%), m.p. 175–177° C., $M^+$ 913.

Preparation of D-12, D-29. and D-31.

These couplers were prepared as described for D-30:

| Coupler | Yield [%] | m.p.[° C.] | $M^+$ |
|---|---|---|---|
| D-12 | 25 | 135-7 | 962 |
| D-29 | 12 | 135-7 | 924 |
| D-31 | 45 | 160-4 | 895 |

Scheme 2. Preparation of D-33.

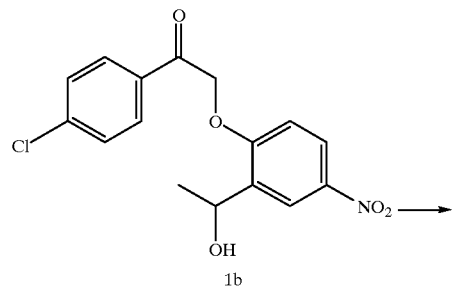

-continued

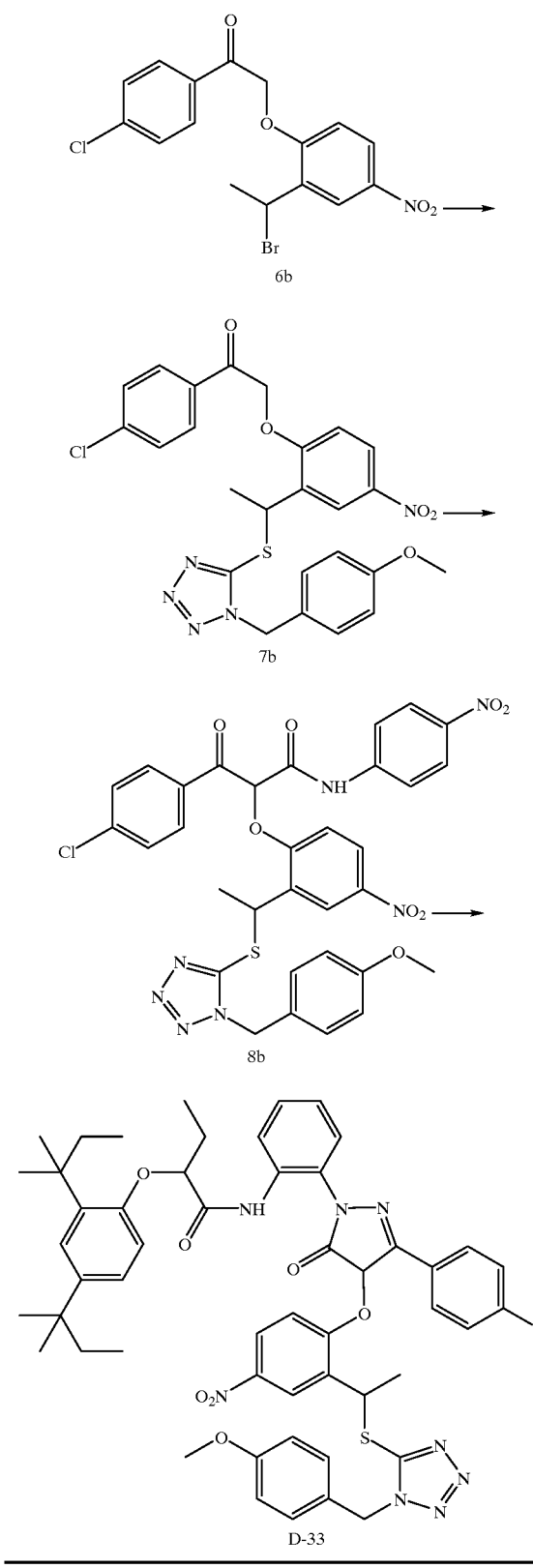

Preparation of 6b.
Triphenylphosphine (26.23 g, 100 mmol) was added in one portion to a solution of 1b (16.79 g, 50 mmol) in 200 mL of dichloromethane, stirred in an ice/water bath. N-Bromosuccinimide (17.80 g, 100 mmol) was then added over a period of 15 min. After a further 45 min at 5° C., the solution was filtered through silica gel. Removal of the solvent gave a solid which was washed with heptanes and dried to give 18.66 g (47 mmol, 94%) of 6b.

Preparation of 7b.
Solid sodium bicarbonate (4.62 g, 55 mmol) was added to a mixture of 6b (19.93 g 50 mmol), 1-(4'-methoxybenzyl)-5-mercaptotetrazole (12.22 g. 55 mmol), and tetra-n-butylammonium bromide (1g) in 250 mL water/250 mL dichloromethane. The mixture was stirred for 5 h, worked up with ethyl acetate/water and the crude product recrystallized from ethanol. The yield of 7b was 26.03 g (48 mmol, 96%).

Preparation of 8b.
Prepared from 7b (21.60 g, 40 mmol), pyrrolidine (10 mL), and 4-nitrophenyl isocyanate (6.56 g, 40 mmol) as described for 3b and 4b. The yield of 8b was 21.84 g (31 mmol, 78%).

Preparation of D-33.
The procedure used to prepare D-30 was followed beginning with 8b (21.12 g. 30 mmol) and 5 (17.33 g, 33 mmol). The yield of D-33 was 9.83 g (10 mmol, 34%), m.p. 164–167° C., M+ 973.

Scheme 3.
Preparation of D-34 and D-35.

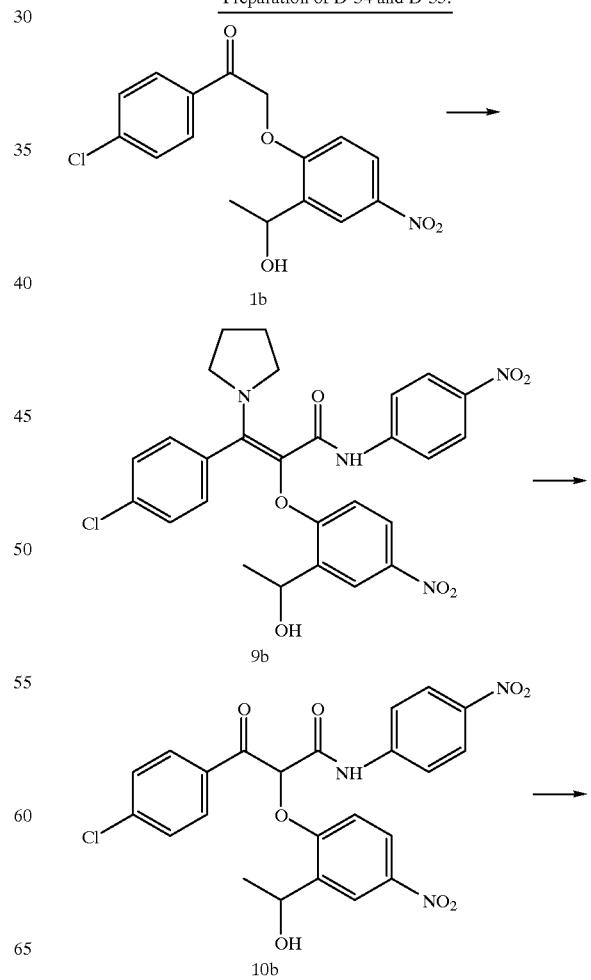

-continued

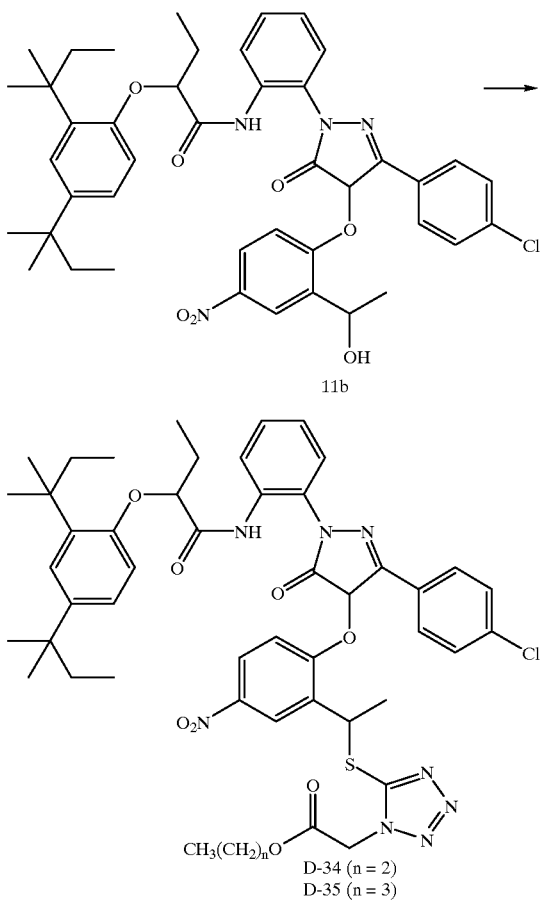

11b

D-34 (n = 2)
D-35 (n = 3)

Preparation of 9b.

A solution of pyrrolidine (20 mL, 288 mmol) and 2b (26.86 g, 80 mmol) in 200 mL of toluene was refluxed for 3 h using a Dean-Stark trap to collect ca. 1.2 mL of water. The solvent and excess pyrrolidine were distilled off. The residue was dissolved in 200 mL of toluene, 4-nitrophenyl isocyanate (13.13 g, 80 mmol) was added, the mixture refluxed for 20 min, stirred at room temperature for 20 h and filtered. The solid product was washed with toluene (200 mL) and dried to produce 34.38 g of 9b (62 mmol, 78%).

Preparation of 10b.

A mixture of 9b (30.48 g, 55 mmol) and concentrated hydrochloric acid (15 mL) in ethanol (300 mL) was refluxed for 4.5 h, cooled and the solvent was distilled off giving an oily residue that was worked up with ethyl acetate and water. The crude product was recrystallized from isopropyl ether and again from ethanol. The yield of 10b was 18.42 g (37 mmol, 67%).

Preparation of 11b.

The procedure used to prepare D-30 was followed beginning with 10b (15.00 g, 30 mmol) and 5 (17.33 g, 33 mmol). The yield of 11b was 6.60 g (8.6 mmol 29%),, $M^+$ 769.

Preparation of D-34.

A solution of 11b (5.67 g, 7.4 mmol), propyl 5'-mercaptotetrazolylacetate (1.90 g, 9.4 mmol), and zinc iodide (1.50 g, 4.7 mmol) in 20 mL of 1,2-dichloroethanol was refluxed for 10 h. The reaction mixture was worked up with propyl acetate and 5% hydrochloric acid. The crude product was purified by column chromatography and finally recrystallized from isopropyl ether. The yield of D-34 was 4.60 g (4.8 g, 65%), m.p. 153–156° C., $M^+$ 953.

Preparation of D-35.

Prepared from 11b (10.77 g, 14 mmol), butyl 5'-mercaptotetrazolylacetate (4.33 g, 20 mmol), and zinc iodide (3.19 g, 10 mmol) as described for D-35. The yield of D-35 was 10.68 g (11 mmol, 79%), m.p. 158–159° C., $M^+$ 967.

PHOTOGRAPHIC EXAMPLES

To illustrate the advantageous behavior of the photographic elements and couplers of this invention, the comparative and inventive couplers used for the photographic examples were evaluated in the multilayer causer/receiver format shown in Table 1. Structures of components that were not given previously are provided after Table I. Component laydowns in $g/m^2$ (unless otherwise noted) are shown in Table I in parentheses. The DIR couplers were each coated at the level (Z, in $mmole/m^2$) cited in the respective example. Each DIR coupler was dispersed at a 1:2 weight ratio in tritolyl phosphate (S-1, mixed isomers). The dispersions were prepared by adding an oil phase containing a 1:2:3 weight ratio of DIR coupler: S-1:ethyl acetate to an aqueous phase containing gelatin and ALKANOL XC(mixed isomers of triisopropyl-2-naphthalene sulfonic acid sodium salt, DuPont) in a 10:1 weight ratio. The mixture was then passed through a colloid mill to disperse the oil phase in the aqueous phase as small particles. On coating, the ethyl acetate evaporates.

To evaluate the photographic performance, film samples were given a sensitometric white light (neutral) exposure and processed in a KODAK FLEXICOLOR C-41 process as in Table II. Green (causer) and red (receiver) status M densities were measured for the samples. Green and red gamma (γ) values were then obtained from slopes of plots of density vs. log exposure. It is desirable that a DIR coupler efficiently reduce gamma or contrast in the layer or color record in which it is coated to effectively provide benefits such as sharpness, reduced granularity and improved exposure latitude. For high interlayer interimage and high color correction it is desirable to that a DIR coupler also efficiently produce gamma reductions in receiver layers without excessive gamma reduction in its own causer layer. In this case, green gamma corresponds to causer gamma and red gamma corresponds to receiver gamma.

To evaluate the raw stock stability of the DIR couplers, film samples were subjected to an accelerated raw stock-keeping test. The test consisted of storage of unexposed, unprocessed film samples at 100° F. and 50% relative humidity for 4 weeks. Samples were then analyzed by analytical hplc for quantity of DIR coupler. Film samples that were stored in a freezer were analyzed similarly. The ratio of the quantity of DIR coupler remaining after keeping to the quantity of DIR coupler in the freezer check was used as a measure of the raw stock stability of the DIR coupler in a film element and is referred to as % DIR Coupler Remaining, or %R:

$\%R = [(\text{Quantity } DIR_{incubated})/(\text{Quantity } DIR_{freezer})] \times 100$ This higher the number, the more stable the coupler. Preferred raw stock keeping for DIR couplers is 95 or better, with a value of 85 being acceptable.

TABLE I

OVERCOAT:Gelatin(5.38)

Bis(vinylsulfonylmethyl)ether Hardener(0.281)
CAUSER:M-1(0.560)& S-1(0.504)& ST-1(0.056)
 DIR Coupler(Z mmole/m²)& S-1(2X weight of DIR)
 Green-Sensitized 0.46 μm Silver Iodobromide
 Emulsion(1.61)

Gelatin(2.69)
INTERLAYER:IS-1(0.054)& S-1(0.054)

Gelatin(0.86)
RECEIVER:CC-1(0.646)& S-2(Dibutyl phthalate, 0.646)
 Red sensitized 0.46 μm Silver Iodobromide
 Emulsion(0.161)
 Tetraazaindene(0.038)

Gelatin(2.69)
Cellulose Acetate Support with Gelatin U-Coat and Antihalation Backing M-1
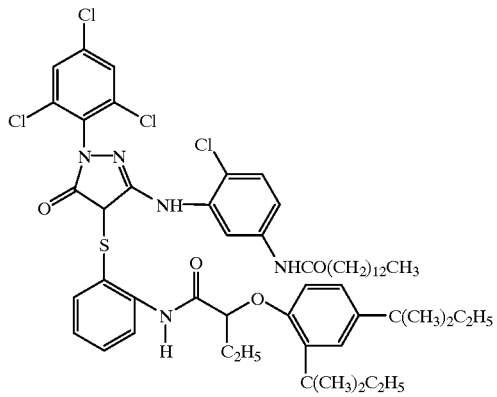

ST-1
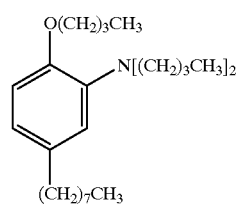

TABLE I-continued

IS-1
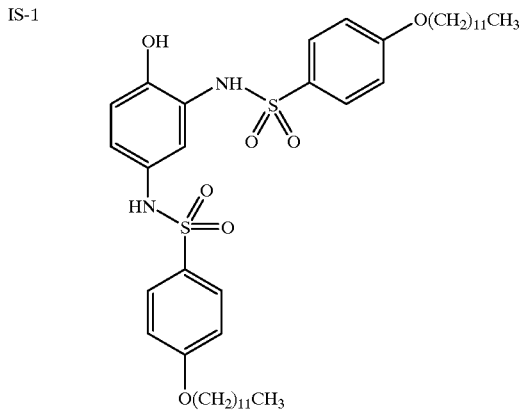

TABLE II

| C-41 Processing Solutions and Conditions | | |
|---|---|---|
| Solution | Processing Time | Agitation Gas |
| C-41 Developer | 3'15" | Nitrogen |
| Stop Bath | 30" | Nitrogen |
| Wash | 2'30" | None |
| Bleach | 3'00" | Air |
| Wash | 3'00" | None |
| Fix | 4'00" | Nitrogen |
| Wash | 3'00" | None |
| Wetting Agent Bath | 30" | None |
| Processing temperature 38° C. | | |

In the following examples, the comparative DIR couplers C1, C2, C-3, C-4, C-5, and C-6 were employed:

| COUPLER | FORMULA |
|---|---|
| C-1 | 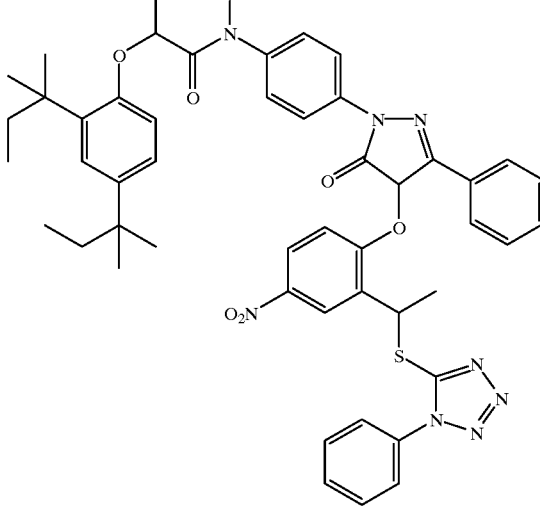 |
| C-2 | 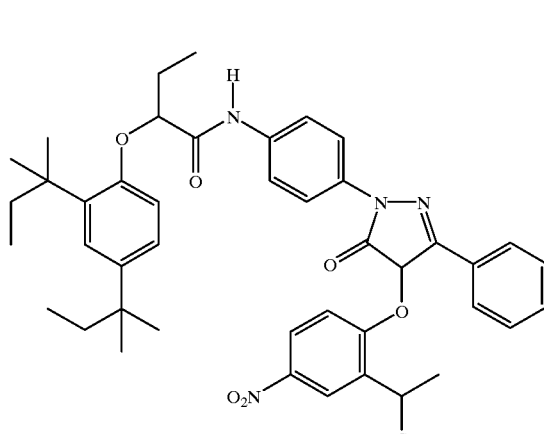 |

| COUPLER | FORMULA |
|---|---|
| C-3 | 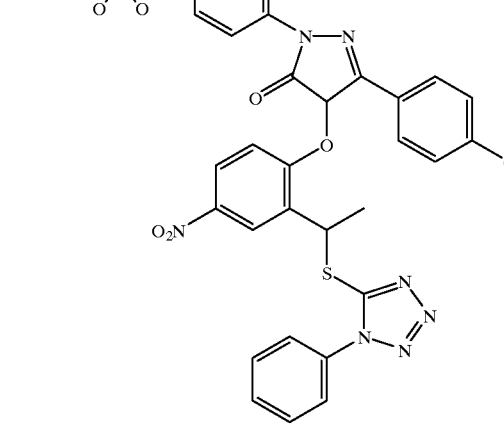 |
| C-4 | 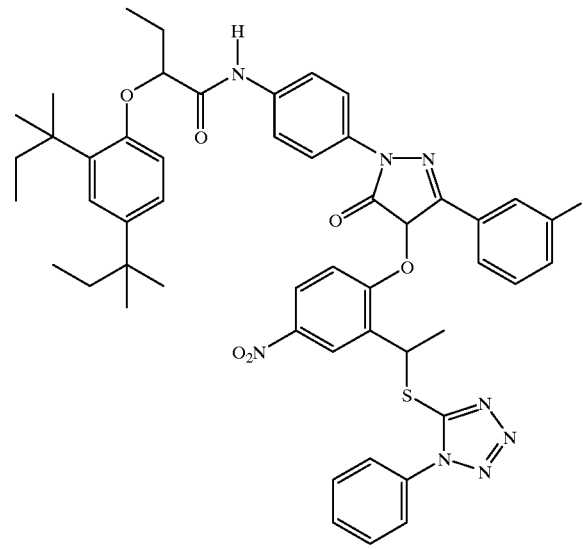 |
| C-5 | 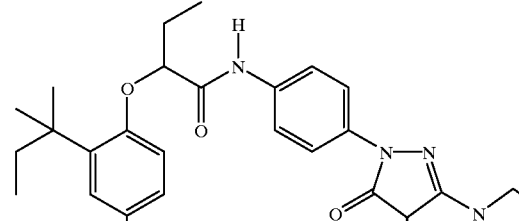 |

| COUPLER | FORMULA |
|---|---|
| C-6 | |

Example 1

Illustration of the Improved Raw Stock Stability in the Photographic Elements of This Invention To illustrate the advantageous behavior of the photographic elements of this invention, inventive couplers D-12, D-13, D-14, D-15, D-16, D-28, D-29, D-30, D-31, D-32, D-33, and D-34 of this invention were compared to couplers C-5 and C-6 of the prior-art. Comparative DIR coupler C-5 is utilized in to the magenta records of commercial color negative films, Comparative coupler C-6 corresponds to specific coupler D-3 in U.S. Pat. No. 5,670,306.

The couplers were dispersed as noted above and were evaluated in the mulitilayer causer/receiver format shown in Table I (Z=0.129). Their raw stock stability was determined as described and is summarized in Table III.

TABLE III

Raw Stock Stability

| Coupler | Type | % R[1] |
|---|---|---|
| C-5 | Comp | 95 |
| C-6 | Comp | 93 |
| D-12 | Inv | 99 |
| D-13 | Inv | 97 |
| D-14 | Inv | 100 |
| D-15 | Inv | 98 |
| D-16 | Inv | 98 |
| D-28 | Inv | 98 |
| D-29 | Inv | 97 |
| D-30 | Inv | 96 |
| D-31 | Inv | 88 |
| D-32 | Inv | 95 |
| D-33 | Inv | 97 |
| D-34 | Inv | 94 |

[1]Keeping results are based on 4 weeks @ 100° F.

The novel couplers in table III were all ortho-substituted on the nitrogen-1-phenyl as described in the invention. All are remarkably stable with most of the inventive DIR couplers in the highly preferred raw stock stability range. Varying substituents in the nitrogen-1 position while the substituents at carbon-4 and carbon-3 remain unchanged (D-13 vs. D-14 vs. D-15 vs. D15) has little effect on overall stability. Varying the substituents at the carbon-3 position (D12 to D16 to D-28 to D-29 to D-30 to D-31 to D-32) surprisingly also has only minor effects and is independent of electron withdrawing or donating effects of these groups. In addition, varying the development inhibitor on the coupling off group on carbon-4 (D-16 to D-33 to D-34) also remarkably has small effects. Furthermore all of the inventive materials compare very favorably to the prior art materials, C-5 and C-6.

Example 2

To further illustrate the advantageous behavior of the photographic elements of this invention, novel DIR couplers of this invention D-13, D-16, D-28., and D-29 were compared to couplers C 1, C-2, C-3, C-4, C-5, and C-6. Comparative DIR coupler C-5 is utilized in the magenta records of commercial color negative films. Comparative coupler C-6 corresponds to specific coupler D-3 in U.S. Pat. No. 5,670,306.

The couplers were dispersed as noted above and were evaluated in the multilayer causer/receiver format shown in Table I (Z=0.129). Their raw stock stability was determined as described and is summarized in Table IV.

TABLE IV

Raw Stock Stability

| Coupler | Type | Substitution | Σσ(Q) | Σσ(P) | % R[1] |
|---|---|---|---|---|---|
| C-5 | Comp | — | — | — | 95 |
| C-6 | Comp | — | — | — | 93 |
| C-2 | Comp | para | −0.28 | 0.91 | * |
| C-4 | Comp | para | 0.11 | 0.91 | 85 |
| C-3 | Comp | para | 0.23 | 0.91 | 99 |
| C-1 | Comp | para | 0.23 | 0.91 | 94 |
| D-29 | Inv | ortho | −0.28 | 0.91 | 97 |

TABLE IV-continued

Raw Stock Stability

| Coupler | Type | Substitution | Σσ(Q) | Σσ(P) | % R[1] |
|---|---|---|---|---|---|
| D-28 | Inv | ortho | 0.11 | 0.91 | 98 |
| D-13 | Inv | ortho | 0.23 | 0.91 | 97 |
| D-16 | Inv | ortho | 0.23 | 0.91 | 98 |

[1]Keeping results are based on 4 weeks @ 100° F.
*This material could not be tested in film-keeping tests because of its instability in air The novel materials D-13, D-16, D-28, and D-29 are all ortho couplers of our invention. The comparative couplers C-1, C-2, C-3, and C-4 are all para materials with D-29 vs. C-2, D-28 vs. C-4, D-13 vs. C-3, and D-16 vs. C-1 representing pairs of DIR couplers that vary only in ortho vs. para substitution as described by our invention. In all cases the ortho material is stable, with %R being in the preferred range. In two of the examples—C-2 vs. D-29, and C-4 vs. D-28 the stability has gone from unacceptable and barely acceptable to preferred. In the case of C-2 vs. D-29 an isolable synthetic, but air unstable, material has surprisingly been made very stable by switching from para to ortho substitution. Even the strong destabilizing effect of the electron donating para-methoxy group in C-2 has been overcome by use of our inventive DIR coupler D-29. Further, all inventive couplers perform well in comparison to the prior art materials C-5 and C-6.

Example 3
Illustration of the Improved Development Inhibition Efficiency in the Photographic Elements of This Invention In this example, coupler D-29 and D-31 of this invention were compared to coupler C-1 of the prior art. Comparative DIR coupler C-1 is utilized in the magenta records of commercial color negative films.

The couplers were dispersed as noted above and were evaluated in the multilayer causer/receiver format shown in Table I (Z=0.129). An additional coating (Z=0.0)(no DIR) was included for comparison. The coatings containing no DIR coupler, coupler C-1, coupler D-29, and coupler D-31, respectively, were given a sensitometric white light exposure (neutral), processed in a KODAK FLEXICOLOR C-41 process, and analyzed as described above. Green (causer) and red (receiver) gamma values obtained from the processed films are shown in Table V.

TABLE V

| Coupler | Type | Green γ | Red γ |
|---|---|---|---|
| None | — | 2.48 | 2.00 |
| C-1 | Comp | 1.08 | 1.37 |
| D-29 | Inv | 1.14 | 0.78 |
| D-31 | Inv | 1.10 | 1.03 |

From the data in Table V, it is apparent that couplers D-29 and D-31 of this invention provide similar reduction in green gamma to comparative coupler C-1 at equimolar laydowns. Thus, in addition to being stable, D-29 and D-31 provide photographic elements in which the DIR coupler can efficiently produce the benefits of sharpness, granularity, and exposure latitude associated with gamma reduction in its own layer.

Furthermore, surprisingly, couplers D-29 and D-31 of this invention also more efficiently produce red gamma reduction in the in the receiver layer, which leads to more efficient color correction via interlayer interimage.

Example 4
Multilayer Film Structure Comprising a Magenta DIR Coupler of This Invention The multilayer film structure utilized for this example is shown schematically in Table VI. Structures of components not provided previously are given immediately following Table VI. Component laydowns are provided in units of g/sq m unless otherwise indicated. This composition may also be coated on a support, such as polyethylene naphthalate, containing a magnetic recording layer. The use of the 3-aryl-4-aryloxypyrazol-5-one DIR coupler D-16 of this invention provides improved sharpness and interlayer interimage. The color negative film described in Table VI may be processed using KODAK FLEXICOLOR C-41 chemistry.

TABLE VI

| MULTILAYER FILM STRUCTURE | |
|---|---|
| 1 Overcoat & UV Layer: | Matte Bead |
| | UV Absorbers UV-1 (0.108), UV-2 (0.108) & S-1 (0.151) |
| | Silver Bromide Lippmann Emulsion (0.215 Ag) |
| | Gelatin (1.237) |
| | Bis(vinylsulfonyl)methane Hardener (1.75% of Total Gelatin) |
| 2 Fast Yellow Layer: | Y-1 (0.237)Yellow Dye-Forming Coupler & S-1 (0.118) |
| | IR-1 (0.076) DIR Coupler & S-1 (0.038) |
| | B-1 (0.0054) BARC & S-3 (0.0070) |
| | Blue Sensitive Silver Iodobromide Emulsion (0.377 Ag), 4.1 mole % Iodide T-Grain (2.9 × 0.12 μm) |
| | Blue Sensitive Silver Iodobromide Emulsion (0.108 Ag) 4.1 mole % Iodide T-Grain (1.9 × 0.14 μm) |
| | Gelatin (0.807) |
| 3 Slow Yellow Layer: | Y-1 (1.076) & S-1 (0.538) |
| | IR-1 (0.076) & S-1 (0.038) |
| | B-1 (0.022) & S-3 (0.028) |
| | CC-1 (0.032) & S-2 (0.064) |
| | IR-4 (0.032) & S-2 (0.064) |
| | Blue Sensitive Silver Iodobromide Emulsion (0.398 Ag), 4.1 mole % Iodide T-Grain (1.9 × 0.14 μm) |
| | Blue Sensitive Silver Iodobromide Emulsion (0.269 Ag), 1.3 mole % Iodide T-Grain (0.54 × 0.08 μm) |
| | Blue Sensitive Silver Iodobromide Emulsion (0.247 Ag) |

TABLE VI-continued

MULTILAYER FILM STRUCTURE

|  |  |
|---|---|
|  | 1.5 mole % Iodide T-Grain (0.77 × 0.14 μm) |
|  | Gelatin (1.872) |
| 4 Yellow Filter Layer: | R-1 (0.086) & S-2 (0.139) & ST-2 (0.012) |
|  | YD-2 Filter Dye (0.054) |
|  | Gelatin (0.646) |
| 5 Fast Magenta Layer: | M-1(0.064) Magenta Dye-Forming Coupler & S-1 (0.058) & ST-1 (0.0064), Addendum, R-2 (0.009) |
|  | MM-1 (0.054) Masking Coupler & S-1 (0.108) |
|  | D-16 (0.036)Inventive Magenta DIR Coupler & S-1 (0.072) |
|  | B-1 (0.003) & S-3 (0.004) |
|  | Green Sensitive Silver Iodobromide Emulsion (0.484 Ag), 4.0 mole % Iodide T-Grain (1.60 × 0.12 μm) |
|  | Gelatin (1.014) |
| 6 Mid Magenta Layer: | M-1 (0.108) & S-1 (0.097) & ST-1 (0.011) |
|  | MM-1 (0.118) & S-1 (0.236), R-2 (0.015) |
|  | D-16 (0.043) Inventive Magenta DIR Coupler & S-1 (0.086) |
|  | Green Sensitive Silver Iodobromide Emulsion (0.247 Ag), 4.0 mole % Iodide T-Grain (1.20 × 0.11 μm) |
|  | Green Sensitive Silver Iodobromide Emulsion (0.247 Ag) 4.0 mole % Iodide T-Grain (1.00 × 0.12 μm) |
|  | Gelatin (1.216) |
| 7 Slow Magenta Layer: | M-1 (0.269) & S-1 (0.242) & ST-1 (0.027) |
|  | MM-1 (0.086) & S-1 (0.172) |
|  | IR-2 (0.011) & S-2 (0.022) |
|  | Green Sensitive Silver Iodobromide Emulsion (0.344 Ag), 3.5 mole % Iodide T-Grain (0.90 × 0.12 μm) |
|  | Green Sensitive Silver Iodobromide Emulsion (0.129 Ag), 1.5 mole % Iodide T-Grain (0.50 × 0.08 μm) |
|  | Gelatin (1.076) |
| 8 Interlayer: | R-1 (0.086) Interlayer Scavenger, S-2 (0.139) & ST-2 (0.012) |
|  | Gelatin (0.538) |
| 9 Fast Cyan Layer: | CC-1 (0.183) Cyan Dye-Forming Coupler & S-2 (0.210) |
|  | CM-1 (0.022) Masking Coupler |
|  | IR-4 (0.027) DIAR Coupler & S-2 (0.054) |
|  | Red Sensitive Silver Iodobromide Emulsion (0.592 Ag), 4.1 mole % Iodide T-Grain (1.7 × 0.12 μm) |
|  | Gelatin (0.915) |
| 10 Mid Cyan Layer: | CC-1 (0.170) & S-2 (0.190) |
|  | CM-1 (0.032) |
|  | B-1 (0.008) & S-3 (0.010) |
|  | IR-4 (0.019) & S-2 (0.038) |
|  | Red Sensitive Silver Iodobromide Emulsion (0.194 Ag), 4.1 mole % Iodide T-Grain (1.2 × 0.11 μm) |
|  | Red Sensitive Silver Iodobromide Emulsion (0.236 Ag), 4.1 mole % Iodide T-Grain (0.91 × 0.11 μm) |
|  | Gelatin (1.076) |
| 11 Slow Cyan Layer: | CC-1 (0.533) & S-2 (0.560) |
|  | IR-4 (0.026) & S-2 (0.052) |
|  | CM-1 (0.032) |
|  | B-1 (0.056) & S-3 (0.073) |
|  | Red Sensitive Silver Iodobromide Emulsion (0.463 Ag), 1.5 mole % Iodide T-Grain (0.54 × 0.06 μm) |
|  | Red Sensitive Silver Iodobromide Emulsion (0.301 Ag) 4.1 mole % Iodide T-Grain (0.53 × 0.12 μm) |
|  | Gelatin (1.679) |
| 12 Antihalation Layer: | Gray Silver (0.135) |
|  | UV-1 (0.075), UV-2 (0.030), S-1 (0.042) S-4 (0.015) |
|  | YD-1 (0.034), MD-1 (0.018) & S-5 (0.018) |
|  | CD-1 (0.025) & S-2 (0.125) |
|  | R-1 (0.161), S-2 (0.261) & ST-2 (0.022) |
|  | Gelatin (2.04) |
| Cellulose Triacetate Support |  |

B-1

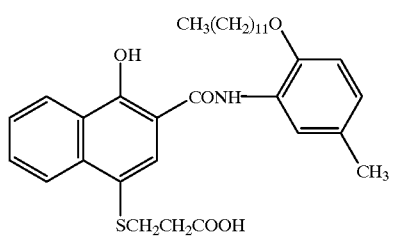

TABLE VI-continued
MULTILAYER FILM STRUCTURE
CC-1
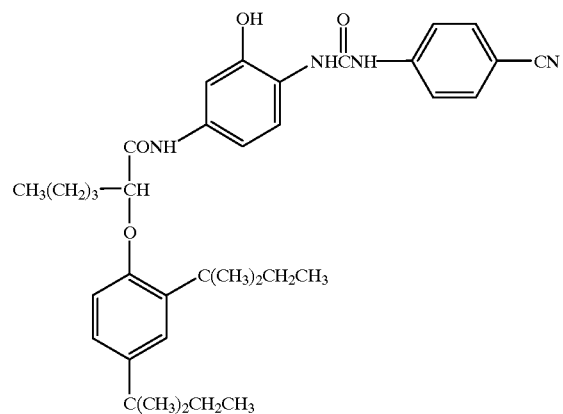
CD-1
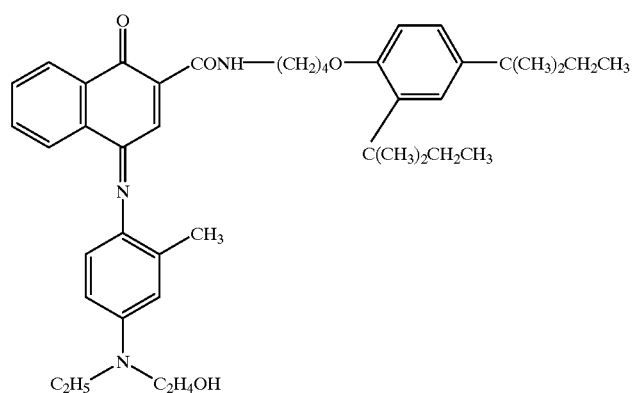
CM-1
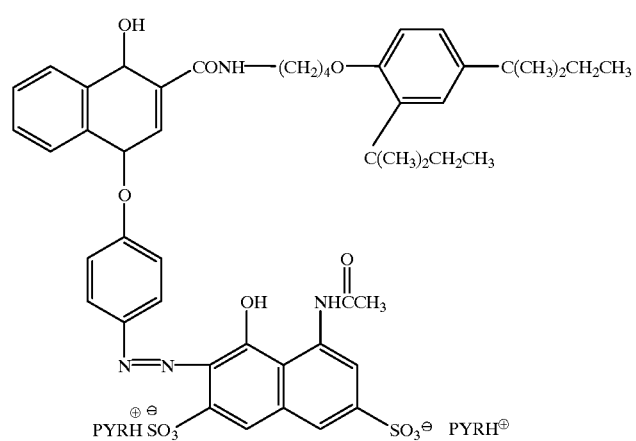

TABLE VI-continued
MULTILAYER FILM STRUCTURE
IR-1
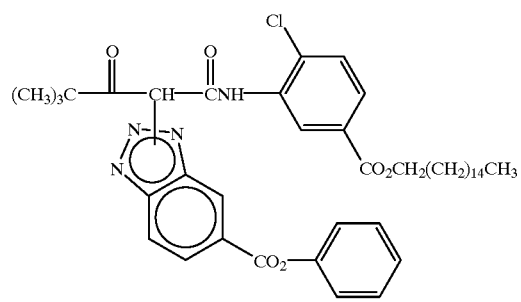
IR-2
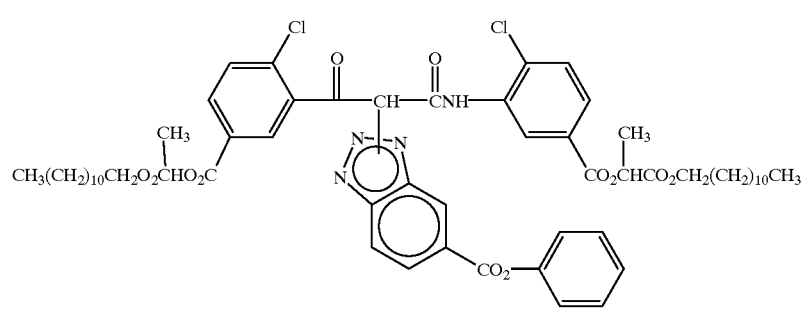
IR-3
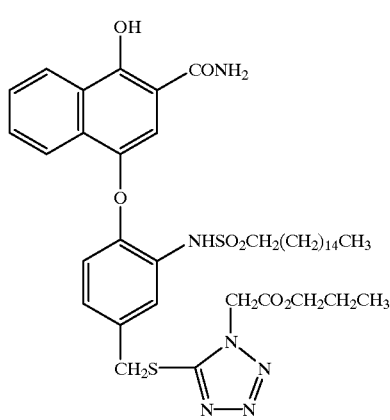
IR-4
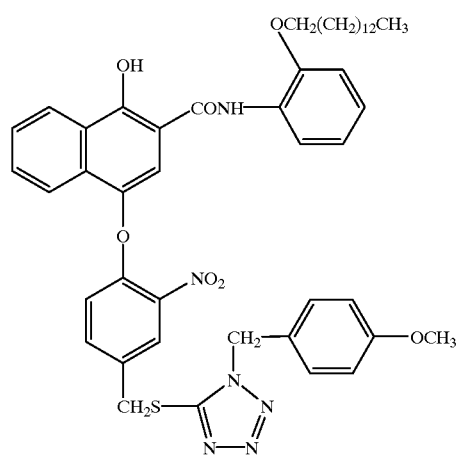

TABLE VI-continued
MULTILAYER FILM STRUCTURE
M-1
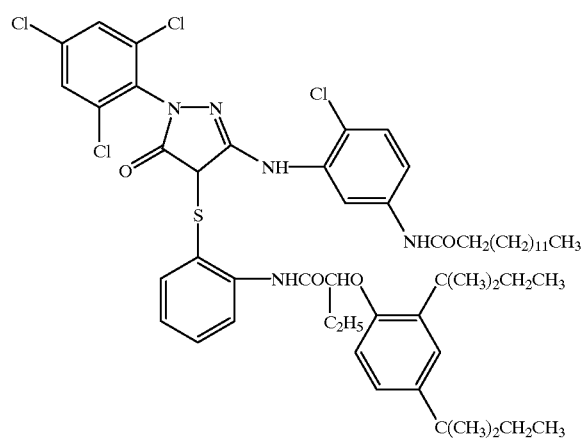
MD-1
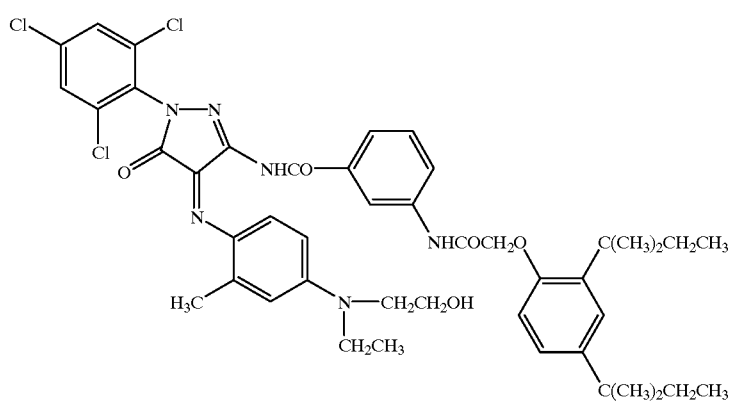
MM-1
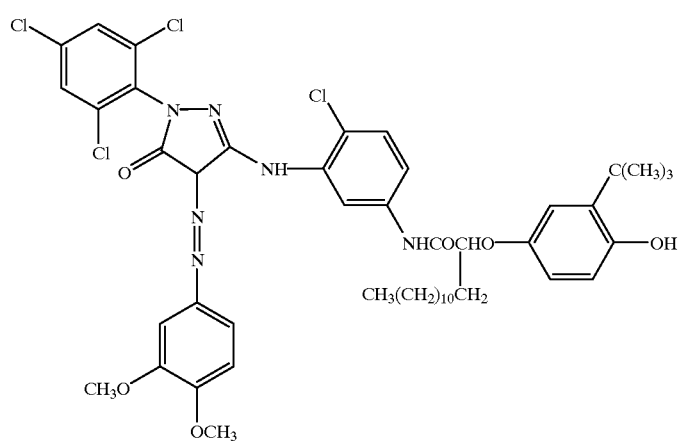
R-1
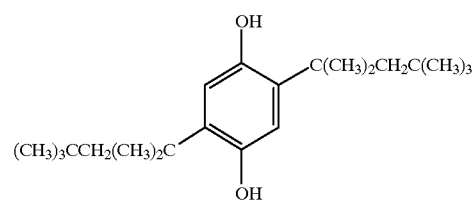

TABLE VI-continued

MULTILAYER FILM STRUCTURE

R-2: 2,4-dihydroxy-5-sulfo-(1-methyl-hexadecyl)benzene structure with OH, CH$_3$, CHCH$_2$(CH$_2$)$_{14}$CH$_3$, HO$_3$S, OH substituents S-1: (H$_3$C–C$_6$H$_4$–O)$_3$P=O, Mixed isomers S-2: benzene-1,2-dicarboxylic acid dibutyl ester, with CO$_2$CH$_2$CH$_2$CH$_2$CH$_3$ groups

S-3: CH$_3$(CH$_2$)$_9$CH$_2$C(=O)—N(C$_2$H$_5$)$_2$

S-4: cyclohexane-1,4-diyl bis(methylene) bis(2-ethylhexanoate): O=C(CH(CH$_2$)$_3$CH$_3$)(C$_2$H$_5$)–O–CH$_2$–[cyclohexane]–CH$_2$–O–C(=O)CH(C$_2$H$_5$)(CH$_2$)$_3$CH$_3$ S-5: (2-ethylhexyl–O)$_3$ P=O ST-1: benzene with OCH$_2$(CH$_2$)$_2$CH$_3$, N(CH$_2$CH$_2$CH$_2$CH$_3$)$_2$, C(CH$_3$)$_2$CH$_2$C(CH$_3$)$_3$ substituents ST-2: 2,6-di-tert-butyl-4-(hexadecyloxycarbonylethyl)phenol: OH, (CH$_3$)$_3$, C(CH$_3$)$_3$, CH$_2$CH$_2$CO$_2$CH$_2$(CH$_2$)$_{14}$CH$_3$

TABLE VI-continued

MULTILAYER FILM STRUCTURE

UV-1
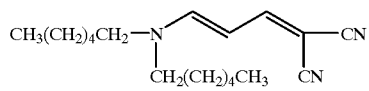

UV-2
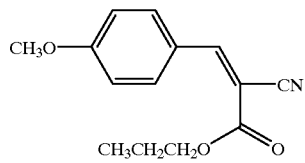

Y-1
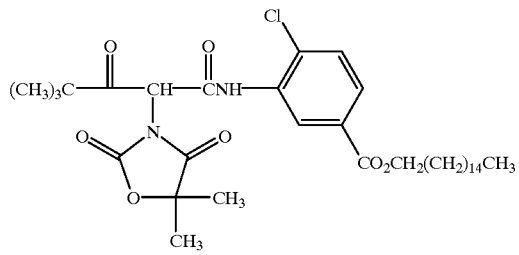

YD-1
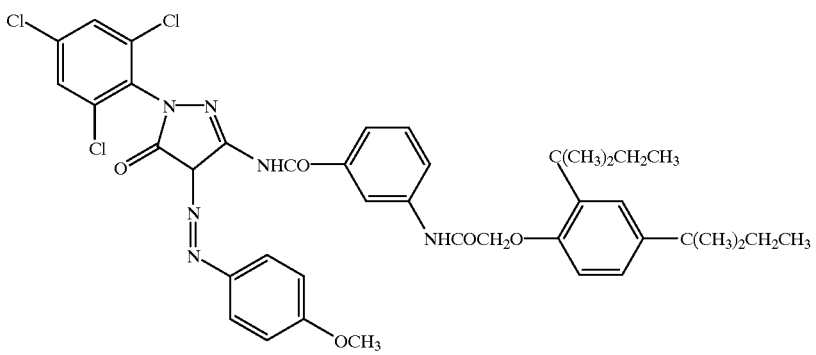

YD-2
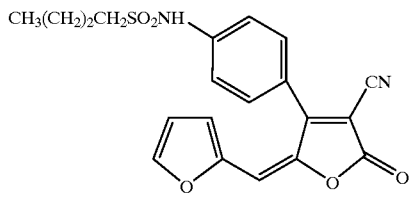

The preceding examples are set forth to illustrate specific embodiments of this invention and are not intended to limit the scope of the compositions, materials or methods of the invention. Additional embodiments and advantages within the scope of the claimed invention will be apparent to one skilled in the art.

The entire contents of the patents and other publications referred to in this specification are incorporated herein by reference.

What is claimed is:

1. A photographic element comprising a light-sensitive silver halide emulsion layer having associated therewith a pyrazol-5-one coupler bearing a 4-aryloxy coupling-off group containing a group capable of releasing a photographically useful group (PUG) wherein:

(1) the pyrazol-5-one ring contains a 1-aryl substituent which in turn contains, in a position ortho to the bond linking it to the pyrazolone ring, a secondary carbonamido group or a secondary sulfonamido group;

(2) the pyrazol-5-one ring contains either (a) a 3-aryl substituent which in turn contains substituents tor which the sum of the Hammett's σ constant values is −0.3 or higher or (b) a 3-alkyl substituent; and (3) the 4-aryloxy coupling-off group:
 (a) contains ring substituents selected so that the sum of the Hammett's σ constant values for all substituents on the phenoxy ring is at least 0.4 but does not contain a nitro substituent in the ortho position, and:
 (b) contains in at least one position ortho or para to the oxygen atom bonding the aryloxy group to the pyrazolone ring a substituent comprising a tetrahedral carbon atom bonded to a PUG or to another timing group which timing group is in turn bonded to a PUG directly or through a further timing group; and provided that substituents may join to form one or more additional rings.

2. The element of claim 1 wherein there is present a 4-aryloxy coupling-off group containing a ring substituent selected from halogen, —NO$_2$, —CN, —NR'SO$_2$R", —NR'C(O)R", —C(O)N(R')R", —C(O)OR', —OC(O)R', —C(O)R', —OSO$_2$R', —SO$_2$R', —SO$_2$N(R')R", —SO$_2$OR' and halogenated alkyl groups wherein each R' and R" is independently hydrogen or a substituent group.

3. The element of claim 2 wherein said 4-aryloxy coupling-off group contains a PUG-containing group in a position ortho to the oxygen atom bonding the aryloxy group to the pyrazolone ring.

4. The element of claim 3 wherein said 4-aryloxy coupling-off group contains an electron withdrawing group in a position para to the oxygen atom bonding the aryloxy group to the pyrazolone ring.

5. The element of claim 1 wherein said 4-aryloxy coupling-off group contains a PUG-containing group in a position para to the oxygen atom bonding the aryloxy group to the pyrazolone ring.

6. The element of claim 5 wherein said 4-aryloxy coupling-off group contains an electron withdrawing group in a position ortho to the oxygen atom bonding the aryloxy group to the pyrazolone ling.

7. The element of claim 1 wherein the 4-aryloxy group is a 4-phenoxy group.

8. The element of claim 1 wherein the coupler has the following formula:

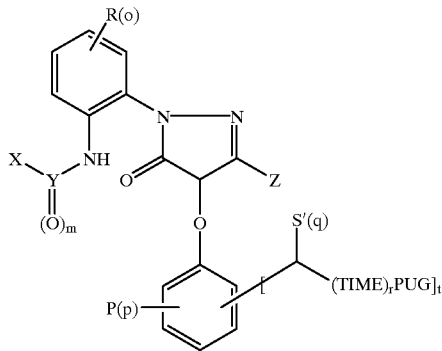

wherein:
X represents an aryl, alkyl, alkylamino or arylamino group;
Y can be carbon or sulfur; m is 1 when Y is carbon and 2 when Y is sulfur;
R represents a halogen or an alkyl group; and o is 0 to 4; provided that two or more R substituents may join to form one or more additional lings;
Z is either (a) an aryl group represented as Ar$^3$Q(n) wherein Q represents n independently selected substituents bonded to the Ar$^3$ ring, provided that the sum of the Hammett's σ constant values for all Q substituents is −0.3 or higher and n is 0 to 5 and provided further that two or more Q substituents may join to form one or more additional rings or (b) an alkyl group;
P represents p independently selected substituents bonded to the aryloxy ring, provided that the sum of the Hammett's σ constant values for all P substituents is at least 0.4, and provided further that P may not be a nitro group ortho to the oxygen atom linking the aryloxy group to the 4 position of the pyrazolone ring and p is 1 to 4, provided that two or more P substituents may join to form one or more additional rings;
each PUG containing substituent is located in a position ortho or para to the oxygen atom bonding the aryloxy group to the pyrazolone ring and t is 1 or 2;
each TIME group is independently a timing group; each r is independently 0 or 1; and each PUG is independently a photographically useful group;
S' represents q independently selected alkyl or aryl groups and q is 0 to 2, provided that two S' groups or an S' and a P group may join to form a ring; and
provided further that X and an R group may join to form an additional ring.

9. The element of claim 8 wherein the 4-aryloxy coupling-off group contains a ring substituent selected from halogen, —NO$_2$, —CN, —NR'SO$_2$R", —NR'C(O)R", —C(O)N(R')R", —C(O)OR', —OC(O)R', —C(O)R', —OSO$_2$R', —SO$_2$R', —SO$_2$N(R')R", —SO$_2$OR' and halogenated alkyl wherein each R' and R" is independently hydrogen or a substituent group.

10. The element of claim 8 wherein said 4-aryloxy coupling-off group contains a PUG-containing group in a position ortho to the oxygen atom bonding the aryloxy group to the pyrazolone ring.

11. The element of claim 10 wherein said 4-aryloxy coupling-off group contains an electron withdrawing group in a position para to the oxygen atom bonding the aryloxy group to the pyrazolone ring.

12. The element of claim 8 wherein said 4-aryloxy coupling-off group contains a PUG-containing group in a position para to the oxygen atom bonding the aryloxy group to the pyrazolone ring.

13. The element of claim 12 wherein said 4-aryloxy coupling-off group contains an electron withdrawing group in a position ortho to the oxygen atom bonding the aryloxy group to the pyrazolone ring.

14. The element of claim 8 wherein the 4-aryloxy group is a phenoxy group.

15. The element of claim 7 wherein the 4-phenoxy group contains a PUG in a position ortho to the oxygen atom bonding the phenoxy group to the pyrazolone ring.

16. The element of claim 15 wherein the 4-phenoxy group contains a nitro group in a position para to the oxygen atom bonding the phenoxy group of the pyrazolone ring.

17. The element of claim 16 wherein the 4-phenoxy group contains a development inhibitor as a PUG.

18. The element of claim 17 wherein the PUG containing group comprises a methyl group attached to the tetrahedral carbon bonding the PUG containing group to the 4-phenoxy group.

* * * * *